United States Patent
Nishiyama

(10) Patent No.: US 10,655,112 B2
(45) Date of Patent: May 19, 2020

(54) POLYPEPTIDE HAVING ENDONUCLEASE ACTIVITY AND METHOD FOR PRODUCING THE SAME

(71) Applicant: KANEKA CORPORATION, Osaka (JP)

(72) Inventor: Tozo Nishiyama, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 16/146,564

(22) Filed: Sep. 28, 2018

(65) Prior Publication Data

US 2019/0017036 A1 Jan. 17, 2019

Related U.S. Application Data

(63) Continuation of application No. PCT/JP2017/012419, filed on Mar. 27, 2017.

(30) Foreign Application Priority Data

Mar. 30, 2016 (JP) ................. 2016-069627

(51) Int. Cl.
| | |
|---|---|
| *C12N 9/44* | (2006.01) |
| *C12N 9/24* | (2006.01) |
| *C12N 9/16* | (2006.01) |
| *C12N 15/09* | (2006.01) |
| *C12N 1/16* | (2006.01) |
| *C12P 21/02* | (2006.01) |
| *C12N 15/52* | (2006.01) |
| *C12N 15/81* | (2006.01) |
| *C07H 21/04* | (2006.01) |

(52) U.S. Cl.
CPC ............. *C12N 9/16* (2013.01); *C12N 1/16* (2013.01); *C12N 15/09* (2013.01); *C12N 15/52* (2013.01); *C12N 15/815* (2013.01); *C12P 21/02* (2013.01)

(58) Field of Classification Search
CPC ......... C12P 21/02; C12N 1/16; C12N 15/815; C12N 15/09; C12N 15/52; C12N 9/16; C12Y 101/01034
USPC .... 435/205, 105, 255, 202, 146, 157, 320.1, 435/252.2
See application file for complete search history.

(56) References Cited

U.S. PATENT DOCUMENTS

| | | |
|---|---|---|
| 5,173,418 A | 12/1992 | Molin et al. |
| 6,365,355 B1 | 4/2002 | McCutchen-Maloney |
| 2012/0135498 A1 | 5/2012 | Greiner-Stoeffele et al. |

FOREIGN PATENT DOCUMENTS

| | | |
|---|---|---|
| CN | 105985968 A | 10/2016 |
| JP | S63-500142 A | 1/1988 |
| WO | 2011/015327 A1 | 2/2011 |
| WO | 2014/131113 A1 | 9/2014 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
K. Biedermann et al. "Purifiation and Characterization of a Serratia Marcescens Nuclease produced by *Escherichia coli*", Carlsberg Research Communications, 1989, vol. 54, No. 1, pp. 17-27 (11 pages).
K. Biedermann et al. "Fermentation Studies of the Secretion of Serratia marcescens Nuclease by *Escherichia coli*", Applied and Environmental Microbiology, 1990, vol. 56, No. 6, pp. 1833-1838 (6 pages).
Accession No. A0A0T9KWKO_9ENTER, UniProt [online], Feb. 17, 2016 (1 page).
T. Yurugi-Kobayashi et al. "Comparison of functional non-glycosylated GPCRs expression in Pichia pastoris", Biochemical and Biophysical Research Communications, 2009, vol. 380, No. 2, pp. 271-276 (6 pages).
S-B. Lee et al. "Expression of the non-glycosylated kringle domain of tissue type plasminogen activator in Pichia and its anti-endothelial cell activity", Protein Expression and Purification, 2006, vol. 50, No. 1, pp. 1-8 (8 pages).
H. Hoshida et al. "N-glycosylation deficiency enhanced heterologous production of a Bacillus licheniformis thermostable a-amylase in *Saccharomyces cerevisiae*", Applied Microbiology and Biotechnology, 2013, vol. 97, No. 12, pp. 5473-5482 (10 pages).
International Search Report issued in International Application No. PCT/JP2017/012419, dated Jun. 20, 2017 (3 pages).
Database UniProt [Online] Mar. 4, 2015, XP002793852 (2 pages).
Extended European Search Report issued in European Application No. 17774955.3, dated Sep. 13, 2019 (5 pages).

* cited by examiner

*Primary Examiner* — Robert B Mondesi
*Assistant Examiner* — Mohammad Y Meah
(74) *Attorney, Agent, or Firm* — Osha Liang LLP

(57) ABSTRACT

A polypeptide includes an amino acid sequence selected from the group consisting of: an amino acid sequence having at least 85% sequence identity to the amino acid sequence of SEQ ID NO: 1; and an amino acid sequence derived from the amino acid sequence of SEQ ID NO: 1 by substitution, deletion, and/or addition of one or more amino acid residues. A yeast host expressing the polypeptide in a secretory production system does not add an N-linked sugar chain to the polypeptide, and the polypeptide has endonuclease activity.

9 Claims, 2 Drawing Sheets

Specification includes a Sequence Listing.

SEQUENCE LISTING

<160> NUMBER OF SEQ ID NOS: 106

<210> SEQ ID NO 1
<211> LENGTH: 245
<212> TYPE: PRT
<213> ORGANISM: Serratia marcescens

<400> SEQUENCE: 1

```
Asp Thr Leu Glu Ser Ile Asp Asn Cys Ala Val Gly Cys Pro Thr Gly
1               5                   10                  15

Gly Ser Ser Asn Val Ser Ile Val Arg His Ala Tyr Thr Leu Asn Asn
                20                  25                  30

Asn Ser Thr Thr Lys Phe Ala Asn Trp Val Ala Tyr His Ile Thr Lys
            35                  40                  45

Asp Thr Pro Ala Ser Gly Lys Thr Arg Asn Trp Lys Thr Asp Pro Ala
        50                  55                  60

Leu Asn Pro Ala Asp Thr Leu Ala Pro Ala Asp Tyr Thr Gly Ala Asn
65                  70                  75                  80

Ala Ala Leu Lys Val Asp Arg Gly His Gln Ala Pro Leu Ala Ser Leu
                85                  90                  95

Ala Gly Val Ser Asp Trp Glu Ser Leu Asn Tyr Leu Ser Asn Ile Thr
            100                 105                 110

Pro Gln Lys Ser Asp Leu Asn Gln Gly Ala Trp Ala Arg Leu Glu Asp
        115                 120                 125

Gln Glu Arg Lys Leu Ile Asp Arg Ala Asp Ile Ser Ser Val Tyr Thr
    130                 135                 140

Val Thr Gly Pro Leu Tyr Glu Arg Asp Met Gly Lys Leu Pro Gly Thr
145                 150                 155                 160

Gln Lys Ala His Thr Ile Pro Ser Ala Tyr Trp Lys Val Ile Phe Ile
                165                 170                 175

Asn Asn Ser Pro Ala Val Asn His Tyr Ala Ala Phe Leu Phe Asp Gln
            180                 185                 190

Asn Thr Pro Lys Gly Ala Asp Phe Cys Gln Phe Arg Val Thr Val Asp
        195                 200                 205
```

Glu Ile Glu Lys Arg Thr Gly Leu Ile Ile Trp Ala Gly Leu Pro Asp
    210                 215                 220

Asp Val Gln Ala Ser Leu Lys Ser Lys Pro Gly Val Leu Pro Glu Leu
225                 230                 235                 240

Met Gly Cys Lys Asn
            245

<210> SEQ ID NO 2
<211> LENGTH: 933
<212> TYPE: DNA
<213> ORGANISM: Komagataella pastoris

<400> SEQUENCE: 2

| | | |
|---|---|---|
| aacatccaaa gacgaaaggt tgaatgaaac cttttttgcca tccgacatcc acaggtccat | 60 |
| tctcacacat aagtgccaaa cgcaacagga ggggatacac tagcagcaga ccgttgcaaa | 120 |
| cgcaggacct ccactcctct tctcctcaac acccactttt gccatcgaaa aaccagccca | 180 |
| gttattgggc ttgattggag ctcgctcatt ccaattcctt ctattaggct actaacacca | 240 |
| tgactttatt agcctgtcta tcctggcccc cctggcgagg ttcatgtttg tttatttccg | 300 |
| aatgcaacaa gctccgcatt acacccgaac atcactccag atgagggctt tctgagtgtg | 360 |
| gggtcaaata gtttcatgtt ccccaaatgg cccaaaactg acagtttaaa cgctgtcttg | 420 |
| gaacctaata tgacaaaagc gtgatctcat ccaagatgaa ctaagtttgg ttcgttgaaa | 480 |
| tgctaacggc cagttggtca aaaagaaact tccaaaagtc ggcataccgt ttgtcttgtt | 540 |
| tggtattgat tgacgaatgc tcaaaaataa tctcattaat gcttagcgca gtctctctat | 600 |
| cgcttctgaa ccccggtgca cctgtgccga aacgcaaatg gggaaacacc cgcttttttgg | 660 |
| atgattatgc cattgtctcca cattgtatgc ttccaagatt ctggtgggaa tactgctgat | 720 |
| agcctaacgt tcatgatcaa aatttaactg ttctaacccc tacttgacag caatatataa | 780 |
| acagaaggaa gctgccctgt cttaaacctt ttttttatca tcattattag cttactttca | 840 |
| taattgcgac tggttccaat tgacaagctt ttgattttaa cgactttttaa cgacaacttg | 900 |
| agaagatcaa aaaacaacta attattcgaa acg | 933 |

<210> SEQ ID NO 3
<211> LENGTH: 500
<212> TYPE: DNA
<213> ORGANISM: Komagataella pastoris

<400> SEQUENCE: 3

| | | |
|---|---|---|
| tcaagaggat gtcagaatgc catttgcctg agagatgcag gcttcatttt tgatactttt | 60 |
| ttatttgtaa cctatatagt ataggatttt ttttgtcatt ttgtttcttc tcgtacgagc | 120 |
| ttgctcctga tcagcctatc tcgcagctga tgaatatctt gtggtagggg tttgggaaaa | 180 |
| tcattcgagt ttgatgtttt tcttggtatt tcccactcct cttcagagta cagaagatta | 240 |
| agtgagacgt tcgtttgtgc aagcttcaac gatgccaaaa gggtataata agcgtcattt | 300 |
| gcagcattgt gaagaaaact atgtggcaag ccaagcctgc gaagaatgta ttttaagttt | 360 |
| gactttgatg tattcacttg attaagccat aattctcgag tatctatgat tggaagtatg | 420 |
| ggaatggtga tacccgcatt cttcagtgtc ttgaggtctc ctatcagatt atgcccaact | 480 |
| aaagcaaccg gaggaggaga | 500 |

<210> SEQ ID NO 4
<211> LENGTH: 2644

```
<212> TYPE: DNA
<213> ORGANISM: Komagataella pastoris

<400> SEQUENCE: 4
cctgatgact gactcactga taataaaaat acggcttcag aatttctcaa gactacactc      60
actgtccgac ttcaagtatg acatttccct tgctacctgc atacgcaagt gttgcagagt     120
ttgataattc cttgagtttg gtaggaaaag ccgtgtttcc ctatgctgct gaccagctgc     180
acaacctgat caagttcact caatcgactg agcttcaagt taatgtgcaa gttgagtcat     240
ccgttacaga ggaccaattt gaggagctga tcgacaactt gctcaagttg tacaataatg     300
gtatcaatga agtgattttg gacctagatt tggcagaaag agttgtccaa aggatcccag     360
gcgctagggt tatctatagg accctggttg ataaagttgc atccttgccc gctaatgcta     420
gtatcgctgt gccttttttct tctccactgg gcgatttgaa aagtttcact aatggcggta     480
gtagaactgt ttatgctttt tctgagaccg caaagttggt agatgtgact tccactgttg     540
cttctggtat aatccccatt attgatgctc ggcaattgac tactgaatac gaactttctg     600
aagatgtcaa aaagttccct gtcagtgaaa ttttgttggc gtctttgact actgaccgcc     660
ccgatggtct attcactact ttggtggctg actcttctaa ttactcgttg ggcctggtgt     720
actcgtccaa aaagtctatt ccggaggcta taaggacaca aactggagtc taccaatctc     780
gtcgtcacgg tttgtggtat aaaggtgcta catctggagc aactcaaaag ttgctgggta     840
tcgaattgga ttgtgatgga gactgcttga aatttgtggt tgaacaaaca ggtgttggtt     900
tctgtcactt ggaacgcact tcctgttttg gccaatcaaa gggtcttaga gccatggaag     960
ccaccttgtg ggatcgtaag agcaatgctc cagaaggttc ttataccaaa cggttatttg    1020
acgacgaagt tttgttgaac gctaaaatta gggaggaagc tgatgaactt gcagaagcta    1080
aatccaagga agatatagcc tgggaatgtg ctgacttatt ttattttgca ttagttagat    1140
gtgccaagta cggtgtgacg ttggacgagg tggagagaaa cctggatatg aagtccctaa    1200
aggtcactag aaggaaagga gatgccaagc caggatacac caaggaacaa cctaaagaag    1260
aatccaaacc taaagaagtc ccttctgaag gtcgtattga attgtgcaaa attgacgttt    1320
ctaaggcctc ctcacaagaa attgaagatg cccttcgtcg tcctatccag aaaacggaac    1380
agattatgga attagtcaaa ccaattgtcg acaatgttcg tcaaaatggt gacaaagccc    1440
ttttagaact aactgccaag tttgatggag tcgctttgaa gacacctgtg ttagaagctc    1500
ctttcccaga ggaacttatg caattgccag ataacgttaa gagagccatt gatctctcta    1560
tagataacgt caggaaaattc catgaagctc aactaacgga gacgttgcaa gttgagactt    1620
gccctggtgt agtctgctct cgtttttgcaa gacctattga gaaagttggc ctctatattc    1680
ctggtggaac cgcaattctg ccttccactt ccctgatgct gggtgttcct gccaaagttg    1740
ctggttgcaa agaaattgtt tttgcatctc cacctaagaa ggatggtacc cttaccccag    1800
aagtcatcta cgttgcccac aaggttggtg ctaagtgtat cgtgctagca ggaggcgccc    1860
aggcagtagc tgctatggct tacggaacag aaactgttcc taagtgtgac aaaatatttg    1920
gtccaggaaa ccagttcgtt actgctgcca agatgatggt tcaaaatgac acatcagccc    1980
tgtgtagtat tgacatgcct gctgggcctt ctgaagttct agttattgct gataaatacg    2040
ctgatccaga tttcgttgcc tcagaccttc tgtctcaagc tgaacatggt attgattccc    2100
aggtgattct gttggctgtc gatatgacag acaaggagct gccagaatt gaagatgctg    2160
ttcacaacca agctgtgcag ttgccaaggg ttgaaattgt acgcaagtgt attgcacact    2220
```

```
ctacaaccct atcggttgca acctacgagc aggctttgga aatgtccaat cagtacgctc    2280
ctgaacactt gatcctgcaa atcgagaatg cttcttctta tgttgatcaa gtacaacacg    2340
ctggatctgt gtttgttggt gcctactctc cagagagttg tggagattac tcctccggta    2400
ccaaccacac tttgccaacg tacgatatg cccgtcaata cagcggagtt aacactgcaa     2460
ccttccagaa gttcatcact tcacaagacg taactcctga gggactgaaa catattggcc    2520
aagcagtgat ggatctggct gctgttgaag gtctagatgc tcaccgcaat gctgttaagg    2580
ttcgtatgga gaaactggga cttatttaat tatttagaga ttttaactta catttagatt    2640
cgat                                                                 2644

<210> SEQ ID NO 5
<211> LENGTH: 993
<212> TYPE: DNA
<213> ORGANISM: Serratia marcescens

<400> SEQUENCE: 5
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaaggggta     240
tctctggaga aaagagacac tttggagtcc attgacaact gtgctgttgg ttgtccaact     300
ggtggttctt ccaacgtttc catcgttaga cacgcttaca cttgaacaa caactccact      360 actaagttcg ctaactgggt tgcttaccac atcactaagg atactccagc ttccggtaag     420
actagaaact ggaaaactga cccagctttg aacccagctg atactttggc tccagctgat     480
tacactggtg ctaacgctgc tttgaaggtt gatagaggtc accaagctcc attggcttca     540
ttggctggtg tttctgactg ggagtccttg aactacttgt ccaacatcac tccacagaag     600
tccgacttga atcaaggtgc ttgggctaga ttggaggacc aagagagaaa gttgatcgac     660
agagctgaca tctcctccgt ttacactgtt actggtccat tgtacgagag agacatggga     720
aagttgccag gtactcaaaa ggctcacact atcccatctg cttactggaa ggttatcttc     780
attaacaact ccccagctgt taatcactat gctgctttct tgtttgacca gaacactcca     840
aagggtgctg acttctgtca gttcagagtt actgttgatg agatcgagaa gagaactggt    900
ttgatcatct gggctggttt gccagatgat gttcaggctt ctttgaagtc caagccaggt    960
gttttgccag agttgatggg ttgtaagaac taa                                 993

<210> SEQ ID NO 6
<211> LENGTH: 30
<212> TYPE: DNA
<213> ORGANISM: Artificial Sequence
<220> FEATURE:
<223> OTHER INFORMATION: Multicloning site

<400> SEQUENCE: 6
aagcttggat ccagatcttc tagagaattc                                      30

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
```
ataaggatcc aacatccaaa gacgaaaggt                                               30

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
tataggatcc cgtttcgaat aattagttgt                                               30

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
ataatctaga tcaagaggat gtcagaatgc                                               30

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10
tatatctaga tctcctcctc cggttgcttt                                               30

<210> SEQ ID NO 11
<211> LENGTH: 30
<212> TYPE: DNA
<213> ORGANISM: Artificial Sequence
<220> FEATURE:
<223> OTHER INFORMATION: primer

<400> SEQUENCE: 11
ataagaattc cctgatgact gactcactga                                               30

<210> SEQ ID NO 12
<211> LENGTH: 30
<212> TYPE: DNA
<213> ORGANISM: Artificial Sequence
<220> FEATURE:
<223> OTHER INFORMATION: primer

<400> SEQUENCE: 12
tatagaattc atcgaatcta aatgtaagtt                                               30

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
ataaagatct atgagatttc cttcaatttt                                               30

<210> SEQ ID NO 14
<211> LENGTH: 30
<212> TYPE: DNA

<213> ORGANISM: Artificial Sequence
<220> FEATURE:
<223> OTHER INFORMATION: primer

<400> SEQUENCE: 14
tataagatct ttagttctta caacccatca                       30

<210> SEQ ID NO 15
<211> LENGTH: 33
<212> TYPE: DNA
<213> ORGANISM: Artificial Sequence
<220> FEATURE:
<223> OTHER INFORMATION: primer

<400> SEQUENCE: 15
tctaacgatg gaaacttggg aagaaccacc agt                   33

<210> SEQ ID NO 16
<211> LENGTH: 33
<212> TYPE: DNA
<213> ORGANISM: Artificial Sequence
<220> FEATURE:
<223> OTHER INFORMATION: primer

<400> SEQUENCE: 16
actggtggtt cttcccaagt ttccatcgtt aga                   33

<210> SEQ ID NO 17
<211> LENGTH: 33
<212> TYPE: DNA
<213> ORGANISM: Artificial Sequence
<220> FEATURE:
<223> OTHER INFORMATION: primer

<400> SEQUENCE: 17
gaacttagta gtggattggt tgttcaaagt gta                   33

<210> SEQ ID NO 18
<211> LENGTH: 33
<212> TYPE: DNA
<213> ORGANISM: Artificial Sequence
<220> FEATURE:
<223> OTHER INFORMATION: primer

<400> SEQUENCE: 18
tacactttga acaaccaatc cactactaag ttc                   33

<210> SEQ ID NO 19
<211> LENGTH: 33
<212> TYPE: DNA
<213> ORGANISM: Artificial Sequence
<220> FEATURE:
<223> OTHER INFORMATION: primer

<400> SEQUENCE: 19
gaacttagta gtggagtagt tgttcaaagt gta                   33

<210> SEQ ID NO 20
<211> LENGTH: 33
<212> TYPE: DNA
<213> ORGANISM: Artificial Sequence
<220> FEATURE:
<223> OTHER INFORMATION: primer

<400> SEQUENCE: 20
tacactttga acaactactc cactactaag ttc                   33

<210> SEQ ID NO 21
<211> LENGTH: 33
<212> TYPE: DNA
<213> ORGANISM: Artificial Sequence
<220> FEATURE:
<223> OTHER INFORMATION: primer

<400> SEQUENCE: 21
gaacttagta gtggaagcgt tgttcaaagt gta                              33

<210> SEQ ID NO 22
<211> LENGTH: 33
<212> TYPE: DNA
<213> ORGANISM: Artificial Sequence
<220> FEATURE:
<223> OTHER INFORMATION: primer

<400> SEQUENCE: 22
tacactttga acaacgcttc cactactaag ttc                              33

<210> SEQ ID NO 23
<211> LENGTH: 33
<212> TYPE: DNA
<213> ORGANISM: Artificial Sequence
<220> FEATURE:
<223> OTHER INFORMATION: primer

<400> SEQUENCE: 23
agcgaactta gtagttgggt tgttgttcaa agt                              33

<210> SEQ ID NO 24
<211> LENGTH: 33
<212> TYPE: DNA
<213> ORGANISM: Artificial Sequence
<220> FEATURE:
<223> OTHER INFORMATION: primer

<400> SEQUENCE: 24
actttgaaca acaacccaac tactaagttc gct                              33

<210> SEQ ID NO 25
<211> LENGTH: 33
<212> TYPE: DNA
<213> ORGANISM: Artificial Sequence
<220> FEATURE:
<223> OTHER INFORMATION: primer

<400> SEQUENCE: 25
gttagcgaac ttagtcttgg agttgttgtt caa                              33

<210> SEQ ID NO 26
<211> LENGTH: 33
<212> TYPE: DNA
<213> ORGANISM: Artificial Sequence
<220> FEATURE:
<223> OTHER INFORMATION: primer

<400> SEQUENCE: 26
ttgaacaaca actccaagac taagttcgct aac                              33

<210> SEQ ID NO 27
<211> LENGTH: 33
<212> TYPE: DNA
<213> ORGANISM: Artificial Sequence
<220> FEATURE:

```
<223> OTHER INFORMATION: primer

<400> SEQUENCE: 27
gttagcgaac ttagtaacgg agttgttgtt caa                                33

<210> SEQ ID NO 28
<211> LENGTH: 33
<212> TYPE: DNA
<213> ORGANISM: Artificial Sequence
<220> FEATURE:
<223> OTHER INFORMATION: primer

<400> SEQUENCE: 28
ttgaacaaca actccgttac taagttcgct aac                                33

<210> SEQ ID NO 29
<211> LENGTH: 33
<212> TYPE: DNA
<213> ORGANISM: Artificial Sequence
<220> FEATURE:
<223> OTHER INFORMATION: primer

<400> SEQUENCE: 29
gttagcgaac ttagttctgg agttgttgtt caa                                33

<210> SEQ ID NO 30
<211> LENGTH: 33
<212> TYPE: DNA
<213> ORGANISM: Artificial Sequence
<220> FEATURE:
<223> OTHER INFORMATION: primer

<400> SEQUENCE: 30
ttgaacaaca actccagaac taagttcgct aac                                33

<210> SEQ ID NO 31
<211> LENGTH: 33
<212> TYPE: DNA
<213> ORGANISM: Artificial Sequence
<220> FEATURE:
<223> OTHER INFORMATION: primer

<400> SEQUENCE: 31
gttagcgaac ttagtcaagg agttgttgtt caa                                33

<210> SEQ ID NO 32
<211> LENGTH: 33
<212> TYPE: DNA
<213> ORGANISM: Artificial Sequence
<220> FEATURE:
<223> OTHER INFORMATION: primer

<400> SEQUENCE: 32
ttgaacaaca actccttgac taagttcgct aac                                33

<210> SEQ ID NO 33
<211> LENGTH: 33
<212> TYPE: DNA
<213> ORGANISM: Artificial Sequence
<220> FEATURE:
<223> OTHER INFORMATION: primer

<400> SEQUENCE: 33
gttagcgaac ttagtaccgg agttgttgtt caa                                33
```

<210> SEQ ID NO 34
<211> LENGTH: 33
<212> TYPE: DNA
<213> ORGANISM: Artificial Sequence
<220> FEATURE:
<223> OTHER INFORMATION: primer

<400> SEQUENCE: 34
ttgaacaaca actccggtac taagttcgct aac                          33

<210> SEQ ID NO 35
<211> LENGTH: 33
<212> TYPE: DNA
<213> ORGANISM: Artificial Sequence
<220> FEATURE:
<223> OTHER INFORMATION: primer

<400> SEQUENCE: 35
gttagcgaac ttagtttggg agttgttgtt caa                          33

<210> SEQ ID NO 36
<211> LENGTH: 33
<212> TYPE: DNA
<213> ORGANISM: Artificial Sequence
<220> FEATURE:
<223> OTHER INFORMATION: primer

<400> SEQUENCE: 36
ttgaacaaca actcccaaac taagttcgct aac                          33

<210> SEQ ID NO 37
<211> LENGTH: 33
<212> TYPE: DNA
<213> ORGANISM: Artificial Sequence
<220> FEATURE:
<223> OTHER INFORMATION: primer

<400> SEQUENCE: 37
gttagcgaac ttagtgaagg agttgttgtt caa                          33

<210> SEQ ID NO 38
<211> LENGTH: 33
<212> TYPE: DNA
<213> ORGANISM: Artificial Sequence
<220> FEATURE:
<223> OTHER INFORMATION: primer

<400> SEQUENCE: 38
ttgaacaaca actccttcac taagttcgct aac                          33

<210> SEQ ID NO 39
<211> LENGTH: 33
<212> TYPE: DNA
<213> ORGANISM: Artificial Sequence
<220> FEATURE:
<223> OTHER INFORMATION: primer

<400> SEQUENCE: 39
gttagcgaac ttagtccagg agttgttgtt caa                          33

<210> SEQ ID NO 40
<211> LENGTH: 33
<212> TYPE: DNA
<213> ORGANISM: Artificial Sequence
<220> FEATURE:
<223> OTHER INFORMATION: primer

```
<400> SEQUENCE: 40
ttgaacaaca actcctggac taagttcgct aac                             33

<210> SEQ ID NO 41
<211> LENGTH: 33
<212> TYPE: DNA
<213> ORGANISM: Artificial Sequence
<220> FEATURE:
<223> OTHER INFORMATION: primer

<400> SEQUENCE: 41
gttagcgaac ttagtgttgg agttgttgtt caa                             33

<210> SEQ ID NO 42
<211> LENGTH: 33
<212> TYPE: DNA
<213> ORGANISM: Artificial Sequence
<220> FEATURE:
<223> OTHER INFORMATION: primer

<400> SEQUENCE: 42
ttgaacaaca actccaacac taagttcgct aac                             33

<210> SEQ ID NO 43
<211> LENGTH: 33
<212> TYPE: DNA
<213> ORGANISM: Artificial Sequence
<220> FEATURE:
<223> OTHER INFORMATION: primer

<400> SEQUENCE: 43
gttagcgaac ttagtgatgg agttgttgtt caa                             33

<210> SEQ ID NO 44
<211> LENGTH: 33
<212> TYPE: DNA
<213> ORGANISM: Artificial Sequence
<220> FEATURE:
<223> OTHER INFORMATION: primer

<400> SEQUENCE: 44
ttgaacaaca actccatcac taagttcgct aac                             33

<210> SEQ ID NO 45
<211> LENGTH: 33
<212> TYPE: DNA
<213> ORGANISM: Artificial Sequence
<220> FEATURE:
<223> OTHER INFORMATION: primer

<400> SEQUENCE: 45
gttagcgaac ttagtctcgg agttgttgtt caa                             33

<210> SEQ ID NO 46
<211> LENGTH: 33
<212> TYPE: DNA
<213> ORGANISM: Artificial Sequence
<220> FEATURE:
<223> OTHER INFORMATION: primer

<400> SEQUENCE: 46
ttgaacaaca actccgagac taagttcgct aac                             33

<210> SEQ ID NO 47
<211> LENGTH: 33
```

-continued

<212> TYPE: DNA
<213> ORGANISM: Artificial Sequence
<220> FEATURE:
<223> OTHER INFORMATION: primer

<400> SEQUENCE: 47
gttagcgaac ttagtagcgg agttgttgtt caa                              33

<210> SEQ ID NO 48
<211> LENGTH: 33
<212> TYPE: DNA
<213> ORGANISM: Artificial Sequence
<220> FEATURE:
<223> OTHER INFORMATION: primer

<400> SEQUENCE: 48
ttgaacaaca actccgctac taagttcgct aac                              33

<210> SEQ ID NO 49
<211> LENGTH: 33
<212> TYPE: DNA
<213> ORGANISM: Artificial Sequence
<220> FEATURE:
<223> OTHER INFORMATION: primer

<400> SEQUENCE: 49
gttagcgaac ttagtgtggg agttgttgtt caa                              33

<210> SEQ ID NO 50
<211> LENGTH: 33
<212> TYPE: DNA
<213> ORGANISM: Artificial Sequence
<220> FEATURE:
<223> OTHER INFORMATION: primer

<400> SEQUENCE: 50
ttgaacaaca actcccacac taagttcgct aac                              33

<210> SEQ ID NO 51
<211> LENGTH: 33
<212> TYPE: DNA
<213> ORGANISM: Artificial Sequence
<220> FEATURE:
<223> OTHER INFORMATION: primer

<400> SEQUENCE: 51
gttagcgaac ttagtcatgg agttgttgtt caa                              33

<210> SEQ ID NO 52
<211> LENGTH: 33
<212> TYPE: DNA
<213> ORGANISM: Artificial Sequence
<220> FEATURE:
<223> OTHER INFORMATION: primer

<400> SEQUENCE: 52
ttgaacaaca actccatgac taagttcgct aac                              33

<210> SEQ ID NO 53
<211> LENGTH: 33
<212> TYPE: DNA
<213> ORGANISM: Artificial Sequence
<220> FEATURE:
<223> OTHER INFORMATION: primer

<400> SEQUENCE: 53

```
gttagcgaac ttagtgtcgg agttgttgtt caa                                    33
```

<210> SEQ ID NO 54
<211> LENGTH: 33
<212> TYPE: DNA
<213> ORGANISM: Artificial Sequence
<220> FEATURE:
<223> OTHER INFORMATION: primer

<400> SEQUENCE: 54

```
ttgaacaaca actccgacac taagttcgct aac                                    33
```

<210> SEQ ID NO 55
<211> LENGTH: 33
<212> TYPE: DNA
<213> ORGANISM: Artificial Sequence
<220> FEATURE:
<223> OTHER INFORMATION: primer

<400> SEQUENCE: 55

```
gttagcgaac ttagtacagg agttgttgtt caa                                    33
```

<210> SEQ ID NO 56
<211> LENGTH: 33
<212> TYPE: DNA
<213> ORGANISM: Artificial Sequence
<220> FEATURE:
<223> OTHER INFORMATION: primer

<400> SEQUENCE: 56

```
ttgaacaaca actcctgtac taagttcgct aac                                    33
```

<210> SEQ ID NO 57
<211> LENGTH: 33
<212> TYPE: DNA
<213> ORGANISM: Artificial Sequence
<220> FEATURE:
<223> OTHER INFORMATION: primer

<400> SEQUENCE: 57

```
gttagcgaac ttagttgggg agttgttgtt caa                                    33
```

<210> SEQ ID NO 58
<211> LENGTH: 33
<212> TYPE: DNA
<213> ORGANISM: Artificial Sequence
<220> FEATURE:
<223> OTHER INFORMATION: primer

<400> SEQUENCE: 58

```
ttgaacaaca actccccaac taagttcgct aac                                    33
```

<210> SEQ ID NO 59
<211> LENGTH: 33
<212> TYPE: DNA
<213> ORGANISM: Artificial Sequence
<220> FEATURE:
<223> OTHER INFORMATION: primer

<400> SEQUENCE: 59

```
gttagcgaac ttagtgtagg agttgttgtt caa                                    33
```

<210> SEQ ID NO 60
<211> LENGTH: 33
<212> TYPE: DNA
<213> ORGANISM: Artificial Sequence

```
<220> FEATURE:
<223> OTHER INFORMATION: primer

<400> SEQUENCE: 60
ttgaacaaca actcctacac taagttcgct aac                                33

<210> SEQ ID NO 61
<211> LENGTH: 33
<212> TYPE: DNA
<213> ORGANISM: Artificial Sequence
<220> FEATURE:
<223> OTHER INFORMATION: primer

<400> SEQUENCE: 61
tctaacgatg gaaacgtcgg aagaaccacc agt                                33

<210> SEQ ID NO 62
<211> LENGTH: 33
<212> TYPE: DNA
<213> ORGANISM: Artificial Sequence
<220> FEATURE:
<223> OTHER INFORMATION: primer

<400> SEQUENCE: 62
actggtggtt cttccgacgt ttccatcgtt aga                                33

<210> SEQ ID NO 63
<211> LENGTH: 33
<212> TYPE: DNA
<213> ORGANISM: Artificial Sequence
<220> FEATURE:
<223> OTHER INFORMATION: primer

<400> SEQUENCE: 63
tctaacgatg gaaacagcgg aagaaccacc agt                                33

<210> SEQ ID NO 64
<211> LENGTH: 33
<212> TYPE: DNA
<213> ORGANISM: Artificial Sequence
<220> FEATURE:
<223> OTHER INFORMATION: primer

<400> SEQUENCE: 64
actggtggtt cttccgctgt ttccatcgtt aga                                33

<210> SEQ ID NO 65
<211> LENGTH: 33
<212> TYPE: DNA
<213> ORGANISM: Artificial Sequence
<220> FEATURE:
<223> OTHER INFORMATION: primer

<400> SEQUENCE: 65
gtgtctaacg atgatgggt tggaagaacc acc                                 33

<210> SEQ ID NO 66
<211> LENGTH: 33
<212> TYPE: DNA
<213> ORGANISM: Artificial Sequence
<220> FEATURE:
<223> OTHER INFORMATION: primer

<400> SEQUENCE: 66
ggtggttctt ccaacccatc catcgttaga cac                                33
```

<210> SEQ ID NO 67
<211> LENGTH: 33
<212> TYPE: DNA
<213> ORGANISM: Artificial Sequence
<220> FEATURE:
<223> OTHER INFORMATION: primer

<400> SEQUENCE: 67
agcgtgtcta acgataacaa cgttggaaga acc                                33

<210> SEQ ID NO 68
<211> LENGTH: 33
<212> TYPE: DNA
<213> ORGANISM: Artificial Sequence
<220> FEATURE:
<223> OTHER INFORMATION: primer

<400> SEQUENCE: 68
ggttcttcca acgttgttat cgttagacac gct                                33

<210> SEQ ID NO 69
<211> LENGTH: 33
<212> TYPE: DNA
<213> ORGANISM: Artificial Sequence
<220> FEATURE:
<223> OTHER INFORMATION: primer

<400> SEQUENCE: 69
agcgtgtcta acgatagcaa cgttggaaga acc                                33

<210> SEQ ID NO 70
<211> LENGTH: 33
<212> TYPE: DNA
<213> ORGANISM: Artificial Sequence
<220> FEATURE:
<223> OTHER INFORMATION: primer

<400> SEQUENCE: 70
ggttcttcca acgttgctat cgttagacac gct                                33

<210> SEQ ID NO 71
<211> LENGTH: 33
<212> TYPE: DNA
<213> ORGANISM: Artificial Sequence
<220> FEATURE:
<223> OTHER INFORMATION: primer

<400> SEQUENCE: 71
agcgtgtcta acgatcttaa cgttggaaga acc                                33

<210> SEQ ID NO 72
<211> LENGTH: 33
<212> TYPE: DNA
<213> ORGANISM: Artificial Sequence
<220> FEATURE:
<223> OTHER INFORMATION: primer

<400> SEQUENCE: 72
ggttcttcca acgttaagat cgttagacac gct                                33

<210> SEQ ID NO 73
<211> LENGTH: 33
<212> TYPE: DNA
<213> ORGANISM: Artificial Sequence
<220> FEATURE:
<223> OTHER INFORMATION: primer

```
<400> SEQUENCE: 73
tctaacgatg aaacaccgg aagaaccacc agt                                33

<210> SEQ ID NO 74
<211> LENGTH: 33
<212> TYPE: DNA
<213> ORGANISM: Artificial Sequence
<220> FEATURE:
<223> OTHER INFORMATION: primer

<400> SEQUENCE: 74
actggtggtt cttccggtgt ttccatcgtt aga                               33

<210> SEQ ID NO 75
<211> LENGTH: 33
<212> TYPE: DNA
<213> ORGANISM: Artificial Sequence
<220> FEATURE:
<223> OTHER INFORMATION: primer

<400> SEQUENCE: 75
tctaacgatg aaactgggg aagaaccacc agt                                33

<210> SEQ ID NO 76
<211> LENGTH: 33
<212> TYPE: DNA
<213> ORGANISM: Artificial Sequence
<220> FEATURE:
<223> OTHER INFORMATION: primer

<400> SEQUENCE: 76
actggtggtt cttccccagt ttccatcgtt aga                               33

<210> SEQ ID NO 77
<211> LENGTH: 33
<212> TYPE: DNA
<213> ORGANISM: Artificial Sequence
<220> FEATURE:
<223> OTHER INFORMATION: primer

<400> SEQUENCE: 77
tctaacgatg aaacctcgg aagaaccacc agt                                33

<210> SEQ ID NO 78
<211> LENGTH: 33
<212> TYPE: DNA
<213> ORGANISM: Artificial Sequence
<220> FEATURE:
<223> OTHER INFORMATION: primer

<400> SEQUENCE: 78
actggtggtt cttccgaggt ttccatcgtt aga                               33

<210> SEQ ID NO 79
<211> LENGTH: 33
<212> TYPE: DNA
<213> ORGANISM: Artificial Sequence
<220> FEATURE:
<223> OTHER INFORMATION: primer

<400> SEQUENCE: 79
tctaacgatg aaacagtgg aagaaccacc agt                                33

<210> SEQ ID NO 80
```

<210> SEQ ID NO 80
<211> LENGTH: 33
<212> TYPE: DNA
<213> ORGANISM: Artificial Sequence
<220> FEATURE:
<223> OTHER INFORMATION: primer

<400> SEQUENCE: 80
actggtggtt cttccactgt ttccatcgtt aga         33

<210> SEQ ID NO 81
<211> LENGTH: 33
<212> TYPE: DNA
<213> ORGANISM: Artificial Sequence
<220> FEATURE:
<223> OTHER INFORMATION: primer

<400> SEQUENCE: 81
tctaacgatg gaaacaacgg aagaaccacc agt         33

<210> SEQ ID NO 82
<211> LENGTH: 33
<212> TYPE: DNA
<213> ORGANISM: Artificial Sequence
<220> FEATURE:
<223> OTHER INFORMATION: primer

<400> SEQUENCE: 82
actggtggtt cttccgttgt ttccatcgtt aga         33

<210> SEQ ID NO 83
<211> LENGTH: 33
<212> TYPE: DNA
<213> ORGANISM: Artificial Sequence
<220> FEATURE:
<223> OTHER INFORMATION: primer

<400> SEQUENCE: 83
tctaacgatg gaaacgtggg aagaaccacc agt         33

<210> SEQ ID NO 84
<211> LENGTH: 33
<212> TYPE: DNA
<213> ORGANISM: Artificial Sequence
<220> FEATURE:
<223> OTHER INFORMATION: primer

<400> SEQUENCE: 84
actggtggtt cttcccacgt ttccatcgtt aga         33

<210> SEQ ID NO 85
<211> LENGTH: 33
<212> TYPE: DNA
<213> ORGANISM: Artificial Sequence
<220> FEATURE:
<223> OTHER INFORMATION: primer

<400> SEQUENCE: 85
tctaacgatg gaaactctgg aagaaccacc agt         33

<210> SEQ ID NO 86
<211> LENGTH: 33
<212> TYPE: DNA
<213> ORGANISM: Artificial Sequence
<220> FEATURE:
<223> OTHER INFORMATION: primer

<400> SEQUENCE: 86
actggtggtt cttccagagt ttccatcgtt aga     33

<210> SEQ ID NO 87
<211> LENGTH: 33
<212> TYPE: DNA
<213> ORGANISM: Artificial Sequence
<220> FEATURE:
<223> OTHER INFORMATION: primer

<400> SEQUENCE: 87
tctaacgatg gaaaccatgg aagaaccacc agt     33

<210> SEQ ID NO 88
<211> LENGTH: 33
<212> TYPE: DNA
<213> ORGANISM: Artificial Sequence
<220> FEATURE:
<223> OTHER INFORMATION: primer

<400> SEQUENCE: 88
actggtggtt cttccatggt ttccatcgtt aga     33

<210> SEQ ID NO 89
<211> LENGTH: 33
<212> TYPE: DNA
<213> ORGANISM: Artificial Sequence
<220> FEATURE:
<223> OTHER INFORMATION: primer

<400> SEQUENCE: 89
tctaacgatg gaaacgatgg aagaaccacc agt     33

<210> SEQ ID NO 90
<211> LENGTH: 33
<212> TYPE: DNA
<213> ORGANISM: Artificial Sequence
<220> FEATURE:
<223> OTHER INFORMATION: primer

<400> SEQUENCE: 90
actggtggtt cttccatcgt ttccatcgtt aga     33

<210> SEQ ID NO 91
<211> LENGTH: 33
<212> TYPE: DNA
<213> ORGANISM: Artificial Sequence
<220> FEATURE:
<223> OTHER INFORMATION: primer

<400> SEQUENCE: 91
tctaacgatg gaaaccaagg aagaaccacc agt     33

<210> SEQ ID NO 92
<211> LENGTH: 33
<212> TYPE: DNA
<213> ORGANISM: Artificial Sequence
<220> FEATURE:
<223> OTHER INFORMATION: primer

<400> SEQUENCE: 92
actggtggtt cttccttggt ttccatcgtt aga     33

<210> SEQ ID NO 93
<211> LENGTH: 33
<212> TYPE: DNA

```
<213> ORGANISM: Artificial Sequence
<220> FEATURE:
<223> OTHER INFORMATION: primer

<400> SEQUENCE: 93
tctaacgatg gaaacacagg aagaaccacc agt                              33

<210> SEQ ID NO 94
<211> LENGTH: 33
<212> TYPE: DNA
<213> ORGANISM: Artificial Sequence
<220> FEATURE:
<223> OTHER INFORMATION: primer

<400> SEQUENCE: 94
actggtggtt cttcctgtgt ttccatcgtt aga                              33

<210> SEQ ID NO 95
<211> LENGTH: 33
<212> TYPE: DNA
<213> ORGANISM: Artificial Sequence
<220> FEATURE:
<223> OTHER INFORMATION: primer

<400> SEQUENCE: 95
tctaacgatg gaaacgtagg aagaaccacc agt                              33

<210> SEQ ID NO 96
<211> LENGTH: 33
<212> TYPE: DNA
<213> ORGANISM: Artificial Sequence
<220> FEATURE:
<223> OTHER INFORMATION: primer

<400> SEQUENCE: 96
actggtggtt cttcctacgt ttccatcgtt aga                              33

<210> SEQ ID NO 97
<211> LENGTH: 33
<212> TYPE: DNA
<213> ORGANISM: Artificial Sequence
<220> FEATURE:
<223> OTHER INFORMATION: primer

<400> SEQUENCE: 97
tctaacgatg gaaacgaagg aagaaccacc agt                              33

<210> SEQ ID NO 98
<211> LENGTH: 33
<212> TYPE: DNA
<213> ORGANISM: Artificial Sequence
<220> FEATURE:
<223> OTHER INFORMATION: primer

<400> SEQUENCE: 98
actggtggtt cttccttcgt ttccatcgtt aga                              33

<210> SEQ ID NO 99
<211> LENGTH: 33
<212> TYPE: DNA
<213> ORGANISM: Artificial Sequence
<220> FEATURE:
<223> OTHER INFORMATION: primer

<400> SEQUENCE: 99
tctaacgatg gaaacccagg aagaaccacc agt                              33
```

<210> SEQ ID NO 100
<211> LENGTH: 33
<212> TYPE: DNA
<213> ORGANISM: Artificial Sequence
<220> FEATURE:
<223> OTHER INFORMATION: primer

<400> SEQUENCE: 100
actggtggtt cttcctgggt ttccatcgtt aga        33

<210> SEQ ID NO 101
<211> LENGTH: 33
<212> TYPE: DNA
<213> ORGANISM: Artificial Sequence
<220> FEATURE:
<223> OTHER INFORMATION: primer

<400> SEQUENCE: 101
tctaacgatg gaaacggagg aagaaccacc agt        33

<210> SEQ ID NO 102
<211> LENGTH: 33
<212> TYPE: DNA
<213> ORGANISM: Artificial Sequence
<220> FEATURE:
<223> OTHER INFORMATION: primer

<400> SEQUENCE: 102
actggtggtt cttcctccgt ttccatcgtt aga        33

<210> SEQ ID NO 103
<211> LENGTH: 33
<212> TYPE: DNA
<213> ORGANISM: Artificial Sequence
<220> FEATURE:
<223> OTHER INFORMATION: primer

<400> SEQUENCE: 103
tctaacgatg gaaaccttgg aagaaccacc agt        33

<210> SEQ ID NO 104
<211> LENGTH: 33
<212> TYPE: DNA
<213> ORGANISM: Artificial Sequence
<220> FEATURE:
<223> OTHER INFORMATION: primer

<400> SEQUENCE: 104
actggtggtt cttccaaggt ttccatcgtt aga        33

<210> SEQ ID NO 105
<211> LENGTH: 255
<212> TYPE: DNA
<213> ORGANISM: Saccharomyces cerevisiae

<400> SEQUENCE: 105
atgagatttc cttcaatttt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc catttccaa cagcacaaat      180 aacgggttat tgtttataaa tactactatt gccagcattg ctgctaaaga agaagggta      240 tctctggaga aaaga                                                     255

```
<210> SEQ ID NO 106
<211> LENGTH: 48
<212> TYPE: DNA
<213> ORGANISM: Artificial Sequence
<220> FEATURE:
<223> OTHER INFORMATION: primer

<400> SEQUENCE: 106
tataagatct ttagtgatga tggtggtgat ggttcttaca acccatca            48
```

POLYPEPTIDE HAVING ENDONUCLEASE ACTIVITY AND METHOD FOR PRODUCING THE SAME

TECHNICAL FIELD

One or more embodiments of the present invention relate to a polypeptide having endonuclease activity that is produced as a polypeptide without the N-linked sugar chain via secretory production from a yeast host, a vector comprising a polynucleotide comprising a nucleotide sequence encoding such polypeptide, a yeast comprising a polynucleotide comprising a nucleotide sequence encoding such polypeptide, and a method for producing such polypeptide.

BACKGROUND

As a wild-type endonuclease of *Serratia marcescens*, a polypeptide comprising the amino acid sequence as shown in SEQ ID NO: 1 is known. This endonuclease is capable of degrading single-stranded or double-stranded DNA or RNA, without depending on its nucleotide sequence. Accordingly, such endonuclease is useful in a wide variety of biochemical fields. As with the case of *E. coli*, *Serratia marcescens* is classified as a Gram-negative *bacillus*. Accordingly, methods of producing a wild-type endonuclease derived from *Serratia marcescens* by culturing *E. coli* transformed with a vector comprising a nucleotide sequence encoding the wild-type endonuclease and allowing the endonuclease to be secreted into the culture supernatant have been known (Patent Literature 1; Non Patent Literatures 1 and 2).

CITATION LIST

Patent Literature

Patent Literature 1: JP Patent No. 2,604,365

Non Patent Literature

Non Patent Literature 1: Biedermann, K. et al., Applied and environmental microbiology, Vol. 56, No. 6, pp. 1833-1838, 1990
Non Patent Literature 2: Biedermann. K. et al., Carlsberg Res. Commun., Vol. 54, pp. 17-27, 1989

A yeast species (i.e., *Komagataella pastoris*) has excellent protein expression ability, and it is a methanol utilizing yeast capable of utilizing cost-effective carbon sources that are advantageous from the viewpoint of industrial production. Other yeast species also have excellent protein expression ability and are considered to be useful as hosts for polypeptide mass-production. In the past, however, no attempts concerning secretory production of wild-type endonucleases derived from *Serratia marcescens* using a polypeptide expression system comprising a yeast host, which is an eukaryote, have been made.

SUMMARY

One or more embodiments of the present invention provide a technique for producing a mutant polypeptide of a wild-type endonuclease derived from *Serratia marcescens* using a polypeptide expression system comprising a yeast host.

The present inventors surprisingly found the following. When a wild-type endonuclease derived from *Serratia marcescens* comprising the amino acid sequence as shown in SEQ ID NO: 1 fused with a signal peptide that enables secretion from a yeast is expressed and obtained via secretory production using an expression system comprising a yeast host, the endonuclease produced comprises the N-linked sugar chain added thereto, and the number of the N-linked sugar chain bound thereto is 2 or 1. Thus, the chemical structures of wild-type endonucleases obtained via secretory production by such technique are not uniform.

The present inventors have conducted studies on a technique that enables secretory production of a mutant polypeptide of a wild-type endonuclease derived from *Serratia marcescens* using a polypeptide expression system comprising a yeast host without the addition of the N-linked sugar chain.

(1) A polypeptide that satisfies all of the following conditions (a), (b), and (c):
(a) a polypeptide comprising the amino acid sequence (a1) or (a2):
(a1) an amino acid sequence exhibiting 85% or higher sequence identity to the amino acid sequence as shown in SEQ ID NO: 1; or
(a2) an amino acid sequence derived from the amino acid sequence as shown in SEQ ID NO: 1 by substitution, deletion, and/or addition of one or a plurality of amino acid residues;
(b) a polypeptide that can be obtained via secretory production using a polypeptide expression system comprising a yeast host without addition of an N-linked sugar chain; and
(c) a polypeptide having endonuclease activity.
(2) The polypeptide according to (1), wherein, in the amino acid sequence (a1) or (a2), amino acid residues corresponding to N20 and N33 in the amino acid sequence as shown in SEQ ID NO: 1 are not modified with the N-linked sugar chain.
(3) The polypeptide according to (2), wherein the amino acid sequence in which both the amino acid residues corresponding to N20 and N33 in the amino acid sequence as shown in SEQ ID NO: 1 are not modified with the N-linked sugar chain satisfies at least one of the following conditions (d) and (e):
(d) an amino acid residue corresponding to N20 in the amino acid sequence as shown in SEQ ID NO: 1 is not asparagine; and
(e) an amino acid residue corresponding to S22 in the amino acid sequence as shown in SEQ ID NO: 1 is not serine or threonine, and
satisfies at least one of the following conditions (f) and (g):
(f) an amino acid residue corresponding to S34 in the amino acid sequence as shown in SEQ ID NO: 1 is proline; and
(g) an amino acid residue corresponding to T35 in the amino acid sequence as shown in SEQ ID NO: 1 is not serine or threonine.
(4) The polypeptide according to (3), wherein
the condition (d) is a condition (d1) an amino acid residue corresponding to N20 in the amino acid sequence as shown in SEQ ID NO: 1 is glycine, proline, aspartic acid, glutamic acid, threonine, alanine, valine, histidine, arginine, methionine, isoleucine, leucine, cysteine, tyrosine, or phenylalanine,
the condition (e) is a condition (e1) an amino acid residue corresponding to S22 in the amino acid sequence as shown in SEQ ID NO: 1 is valine, alanine, or lysine, and the condition (g) is a condition (g1) an amino acid residue corresponding to T35 in the amino acid sequence as shown in SEQ ID NO: 1 is lysine, valine, arginine, or leucine, and the polypeptide satisfying at least one of the conditions (d1) and (e1) and at least one of the conditions (f) and (g1).
(5) A vector comprising a polynucleotide comprising a nucleotide sequence encoding the polypeptide according to any of (1) to (4) and a signal peptide that enables secretion of the polypeptide from a yeast.
(6) A yeast comprising a polynucleotide comprising a nucleotide sequence encoding the polypeptide according to any of (1) to (4) and a signal peptide that enables secretion of the polypeptide from a yeast.
(7) A method for producing the polypeptide according to any of (1) to (4) comprising a step of culturing the yeast according to (6).
(8) A polynucleotide encoding the polypeptide according to any of (1) to (4).

This description includes part or all of the content as disclosed in the description and/or drawings of Japanese Patent Application No. 2016-069627, which is a priority document of the present application.

According to one or more embodiments of the present invention, a mutant polypeptide of a wild-type endonuclease derived from *Serratia marcescens* can be obtained via secretory production using a polypeptide expression system comprising a yeast host without the addition of the N-linked sugar chain.

DESCRIPTION OF EMBODIMENTS

Figure 1:
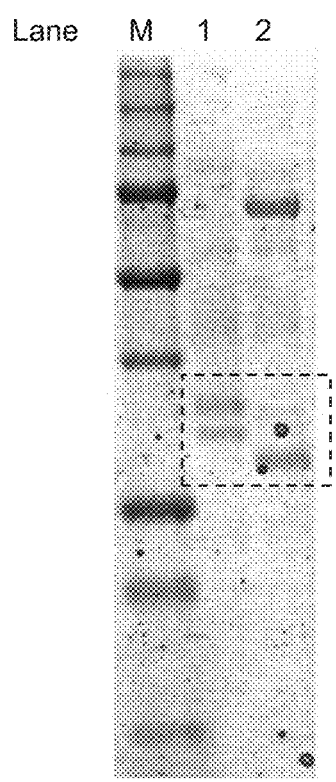
FIG. 1 shows the results of electrophoresis of a wild-type endonuclease secreted in a yeast culture supernatant (lane 1) and of a polypeptide resulting from cleavage of the N-linked sugar chain of the wild-type endonuclease (lane 2).

Hereafter, one or more embodiments of the present invention are described in detail with reference to preferable embodiments.
1. Definition of Terms In one or more embodiments of the present invention, two polynucleotides are hybridized to each other under stringent conditions in the manner described below. For example, a polynucleotide X is fixed to a filter and subjected to hybridization to a polynucleotide Y in the presence of 0.7 to 1.0 M NaCl at 65° C., and the filter is washed with a 2×SSC solution (a 1×SSC solution is composed of 150 mM sodium chloride and 15 mM sodium citrate) at 65° C. When the polynucleotide Y can be obtained as a polynucleotide bound to the filter, the polynucleotide Y can be referred to as "a polynucleotide hybridizing under stringent conditions to the polynucleotide X." Alternatively, it can be said that a polynucleotide X and a polynucleotide Y "hybridizes to each other under stringent conditions." A polynucleotide Y may be obtained in the form of a polynucleotide bound to a filter by washing the filter preferably with a 0.5×SSC solution at 65° C., more preferably with a 0.2×SSC solution at 65° C., and further preferably with a 0.1×SSC solution at 65° C. A reference polynucleotide X may be derived from a colony or plaque.

In one or more embodiments of the present invention, nucleotide sequence and amino acid sequence identity can be determined with the use of a method and sequence analysis software well known to a person skilled in the art. For example, the blastn program or blastp program of the BLAST algorithm or the fasta program of the FASTA algorithm can be used. In the present disclosure, the "sequence identity" between the target nucleotide sequence to be evaluated and the nucleotide sequence X is determined by aligning a nucleotide sequence X and a target nucleotide sequence to be evaluated, introducing a gap according to need, adjusting the degree of nucleotide consistency therebetween at the maximal level, determining a frequency of the identical nucleotides appearing at the identical sites in the nucleotide sequence comprising gap portions, and representing the frequency in terms of percentage (%). When the nucleotide sequence of DNA is compared with the nucleotide sequence of RNA, T and U are regarded as identical to each other. In the present disclosure, "sequence identity" between a target amino acid sequence and an amino acid sequence X is determined by aligning the amino acid sequence X and the target amino acid sequence, introducing a gap according to need, adjusting the degree of amino acid consistency therebetween to the maximal, and indicating a frequency of the identical amino acids appearing at the identical sites in the amino acid sequence containing a gap portion in terms of percentage (%).

In the present disclosure, the term "polynucleotide" can be referred to as a "nucleic acid," the term refers to DNA or RNA, and the term typically refers to DNA. In the present disclosure, a "polynucleotide" may be double-stranded with its complementary strand. When a "polynucleotide" is DNA, in particular, DNA comprising a given nucleotide sequence may be preferably double-stranded with DNA comprising a complementary nucleotide sequence thereof.

In the present disclosure, a "polypeptide" is composed of 2 or more amino acids bound to each other via a peptide bond. A "polypeptide" encompasses, in addition to a protein, a short-stranded peptide or oligopeptide.

In the present disclosure, a "nucleotide sequence encoding" a polypeptide refers to a nucleotide sequence of a polynucleotide that induces polypeptide production via transcription and translation. For example, a nucleotide sequence designed based on the codon listing concerning a polypeptide comprising an amino acid sequence is within the scope of one or more embodiments of the present invention.

The term "host" used herein refers to a cell that is transformed via introduction of a polynucleotide, and it is also referred to as a "host cell" of "transformant."

In the present disclosure, the term "expression" refers to transcription and translation of a nucleotide sequence that generates a polypeptide. Such expression may be substantially constant regardless of external stimuli, growth conditions, and other factors. Alternatively, such expression may vary depending on such factors. A promoter that drives expression is not particularly limited, provided that such promoter drives expression of a nucleotide sequence encoding the polypeptide.

The term "polypeptide expression system" used herein refers to a host into which a polynucleotide comprising a nucleotide sequence encoding a polypeptide has been introduced, and which is capable of expression and secretory production of the polypeptide.

A host organism species may be preferably a yeast herein.

A yeast may not be capable of assimilating methanol, and examples thereof include those of *Saccharomyces, Schizosaccharomyces, Kluyveromyces*, and *Yarrowia*. A yeast may be capable of assimilating methanol, and a yeast capable of assimilating methanol may be more preferable. In general, a methanol utilizing yeast is defined as a yeast that can be cultured with the use of methanol as a single carbon source. A yeast that was originally a methanol utilizing yeast but has lost its methanol assimilability via artificial modification or variation is within the scope of the methanol utilizing yeast in one or more embodiments of the present invention.

Examples of methanol utilizing yeast strains include those of *Pichia, Komagataella, Ogataea, Candida,* and *Torulopsis.* An example of *Pichia* is *Pichia methanolica*, examples of *Komagataella* include *Komagataella pastoris* and *Komagataella phaffii*, examples of *Ogataea* include *Ogataea angusta, Ogataea polymorpha, Ogataea parapolymorpha,* and *Ogataea minuta*, and an example of *Candida* is *Candida boidinii*.

Among the methanol utilizing yeast strains mentioned above, yeast strains of *Pichia, Komagataella*, or *Ogataea* may be particularly preferable.

Yeast strains of *Komagataella* may be preferably *Komagataella pastoris* and *Komagataella phaffii*. *Komagataella pastoris* and *Komagataella phaffii* are also referred to as *Pichia pastoris*.

Specific examples of strains that can be used as hosts include *Komagataella pastoris* ATCC76273 (Y-11430, CBS7435) and *Komagataella pastoris* X-33. These strains are available from, for example, American Type Culture Collection or Thermo Fisher Scientific.

Yeast strains of *Ogataea* may be preferably *Ogataea angusta, Ogataea polymorpha,* and *Ogataea parapolymorpha*. These three strains are related to each other and are also referred to as "*Hansenula polymorpha*" or "*Pichia angusta*."

Specific examples of strains that can be used include *Ogataea angusta* NCYC495 (ATCC 14754), *Ogataea polymorpha* 8V (ATCC34438), and *Ogataea parapolymorpha* DL-1 (ATCC26012). These strains are available from, for example, American Type Culture Collection.

In one or more embodiments of the present invention, strains derived from yeast strains such as those of *Pichia, Komagataella,* and *Ogataea* can be used. An example of a histidine-auxotrophic strain is the *Komagataella pastoris* GS 115 strain (available from Thermo Fisher Scientific), and examples of leucine-auxotrophic strains include BY4329 derived from NCYC495, BY5242 derived from 8V, and BY5243 derived from DL-1 (these strains can be provided by the National BioResource Project). In one or more embodiments of the present invention, strains derived from such strains can also be used.

In the present disclosure, the term "secretory production" refers to production of a polypeptide by a host cell. Specifically, a host cell containing a polynucleotide comprising a nucleotide sequence encoding a polypeptide of interest expresses and secretes the polypeptide extracellularly.

2. The Polypeptide According to One or More Embodiments of the Present Invention When a polypeptide comprising a conserved sequence Asn-X1-X2 (wherein X1 represents an amino acid residue other than proline; and X2 represents serine or threonine) in an amino acid sequence is expressed in a yeast and secreted, the N-linked sugar chain is added to the Asn in the conserved sequence. It should be noted that the presence of the conserved sequence does not always lead to the addition of the N-linked sugar chain to the Asn. Because of the influence of, for example, the three-dimensional structure in the vicinity of the conserved sequence in the polypeptide, the Asn may not be modified with the N-linked sugar chain. In the amino acid sequence of a wild-type endonuclease of *Serratia marcescens* as shown in SEQ ID NO: 1, amino acids 20 to 22 (Asn-Val-Ser), amino acids 32 to 34 (Asn-Asn-Ser), amino acids 33 to 35 (Asn-Ser-Thr), amino acids 110 to 112 (Asn-Ile-Thr), and amino acids 177 to 179 (Asn-Asn-Ser) each correspond to the conserved sequence. The present inventors found that, among the conserved sequences mentioned above, Asn20 (N20) in amino acids 20 to 22 (Asn-Val-Ser) and Asn33 (N33) in amino acids 33 to 35 (Asn-Ser-Thr) would be modified with the N-linked sugar chain, and Asn32, Asn 110, and Asn 177 in other conserved sequences would not be modified with the N-linked sugar chain, when a wild-type endonuclease derived from *Serratia marcescens* is to be obtained via secretory production using an expression system comprising a yeast host. When a wild-type endonuclease derived from *Serratia marcescens* comprising the amino acid sequence as shown in SEQ ID NO: 1 was expressed and produced via secretion using an expression system comprising an *E. coli* host according to a conventional technique, in contrast, the N-linked sugar chain was not added, and chemical structures of the resulting wild-type endonucleases were uniform.

On the basis of the finding described above, the present inventors completed the polypeptide according to one or more embodiments of the present invention described in more detail below as a mutant polypeptide of a wild-type endonuclease derived from *Serratia marcescens* that can be obtained via secretory production using a polypeptide expression system comprising a yeast host without the addition of the N-linked sugar chain.

One or more embodiments of the present invention relate to a polypeptide that satisfies all of the conditions (a), (b), and (c) described above.

Under the condition (a), the polypeptide according to one or more embodiments of the present invention comprises the amino acid sequence (a1) or (a2) below.

(a1) An amino acid sequence exhibiting 85% or higher sequence identity to the amino acid sequence as shown in SEQ ID NO: 1; or (a2) an amino acid sequence derived from the amino acid sequence as shown in SEQ ID NO: 1 by substitution, deletion, and/or addition of one or a plurality of amino acid residues.

The amino acid sequence as shown in SEQ ID NO: 1 is the amino acid sequence of a wild-type endonuclease of *Serratia marcescens*. The amino acid sequence as shown in SEQ ID NO: 1 does not comprise a signal sequence.

The amino acid sequence (a1) or (a2) is occasionally referred to as the "amino acid sequence of the polypeptide according to one or more embodiments of the present invention" herein.

In the amino acid sequence (a1), sequence identity may be preferably 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99% or higher. It should be noted that the amino acid sequence (a1) is a mutant sequence of the amino acid sequence as shown in SEQ ID NO: 1, and sequence identity between the amino acid sequence (a1) and the amino acid sequence as shown in SEQ ID NO: 1 is less than 100%.

In the amino acid sequence (a2), the term "one or a plurality of" refers to, for example, 1 to 40, 1 to 35, 1 to 30, 1 to 25, 1 to 20, 1 to 15, 1 to 10, 1 to 7, 1 to 5, 1 to 4, 1 to 3, or 1 or 2, or 2 to 35, 2 to 30, 2 to 25, 2 to 20, 2 to 15, 2 to 10, 2 to 7, 2 to 5, 2 to 4, or 2 or 3, or 2.

Under the condition (b) above, a polypeptide without the N-linked sugar chain is obtained via secretory production using a polypeptide expression system comprising a yeast host. At least one yeast strain, such as a yeast of *Komagataella* to be used as a host for polypeptide production, may be used. An example of a yeast strain of *Komagataella* is *Komagataella pastoris* (also referred to as "*Pichia pastoris*"). As described above, the present inventors found that, among the conserved sequences mentioned above, Asn20 (N20) in amino acids 20 to 22 (Asn-Val-Ser) and Asn33 (N33) in amino acids 33 to 35 (Asn-Ser-Thr) would be modified with the N-linked sugar chain, and Asn32, Asn110, and Asn177 in other conserved sequences would not be modified with the N-linked sugar chain, when a wild-type endonuclease derived from *Serratia marcescens* is to be obtained via secretory production using an expression system comprising a yeast host. In the polypeptide according to one or more embodiments of the present invention that satisfies the condition (b), an amino acid residue corresponding to Asn in such conserved sequence is not modified with the N-linked sugar chain, and specific embodiments thereof are described below.

Under the condition (c) above, a polypeptide "having endonuclease activity" refers that a polypeptide has enzymatic activity of cleaving a 3',5'-phosphodiester bond in a polynucleotide chain (DNA or RNA) and producing a polynucleotide fragment. Whether or not a polypeptide of interest has endonuclease activity can be determined in the manner described in Example 5. That is, a standard DNA sample is dissolved in an adequate buffer, a polypeptide of interest is added thereto at an adequate temperature (e.g., 37° C.), and whether or not the absorbance of the resulting solution at the wavelength of 260 nm is increased within a given period of time (e.g., 1 minute) after the addition of the polypeptide is examined. The presence of endonuclease activity can be determined on the basis of such increase.

In the polypeptide according to one or more embodiments of the present invention, the amino acid sequence (a1) or (a2) is different from the amino acid sequence as shown in SEQ ID NO: 1, in a manner such that amino acid residues corresponding to asparagine 20 (N20) and asparagine 33 (N33) would not be modified with the N-linked sugar chain. The term "amino acid residues corresponding to N20 and N33 in the amino acid sequence as shown in SEQ ID NO: 1" refers to amino acid residues in the amino acid sequence of the polypeptide according to one or more embodiments of the present invention corresponding to N20 and N33 in the amino acid sequence as shown in SEQ ID NO: 1, when the amino acid sequence as shown in SEQ ID NO: 1 is aligned with the amino acid sequence of the polypeptide according to one or more embodiments of the present invention, so as to maximize the degree of amino acid consistency therebetween. A specific method of alignment is as described with reference to sequence identity. The expression "an amino acid residue corresponding to Xn in the amino acid sequence as shown in SEQ ID NO: 1" used herein refers to an amino acid residue in the amino acid sequence of the polypeptide according to one or more embodiments of the present invention corresponding to an amino acid residue X at position n in the amino acid sequence as shown in SEQ ID NO: 1, when the amino acid sequence as shown in SEQ ID NO: 1 is aligned with the amino acid sequence of the polypeptide according to one or more embodiments of the present invention, so as to maximize the degree of amino acid consistency therebetween.

The polypeptide according to one or more embodiments of the present invention comprises an amino acid sequence in which both the amino acid residues corresponding to N20 and N33 in the amino acid sequence as shown in SEQ ID NO: 1 are not modified with the N-linked sugar chain.

The amino acid sequence of the polypeptide according to one or more embodiments of the present invention preferably satisfies at least one of the conditions (d), (h), and (e) described below, and particularly preferably satisfies at least either the condition (d) or (e), so that the amino acid residue corresponding to N20 in the amino acid sequence as shown in SEQ ID NO: 1 would not be modified with the N-linked sugar chain:

(d) an amino acid residue corresponding to N20 in the amino acid sequence as shown in SEQ ID NO: 1 is not asparagine:

(h) an amino acid residue corresponding to valine 21 (V21) in the amino acid sequence as shown in SEQ ID NO: 1 is proline; and (e) an amino acid residue corresponding to serine 22 (S22) in the amino acid sequence as shown in SEQ ID NO: 1 is not serine or threonine. When such polypeptide is to be obtained via secretory production with the use of a polypeptide expression system comprising a yeast host, a polypeptide comprising an amino acid in which an amino acid residue corresponding to N20 in the amino acid sequence as shown in SEQ ID NO: 1 is not modified with the N-linked sugar chain is obtained, and endonuclease activity in the culture supernatant containing such polypeptide is sufficiently high.

The condition (d) may be preferably a condition (d1): an amino acid residue corresponding to N20 in the amino acid sequence as shown in SEQ ID NO: 1 is glycine, proline, aspartic acid, glutamic acid, threonine, alanine, valine, histidine, arginine, methionine, isoleucine, leucine, cysteine, tyrosine, or phenylalanine.

The condition (e) may be preferably a condition (e1): an amino acid residue corresponding to S22 in the amino acid sequence as shown in SEQ ID NO: 1 is valine, alanine, or lysine.

When the polypeptide according to one or more embodiments of the present invention satisfies at least either the condition (d1) or (e1), endonuclease activity in the culture supernatant containing the polypeptide is particularly high when the polypeptide is obtained via secretory production using a polypeptide expression system comprising a yeast host.

Under the condition (d1), in particular, an amino acid residue corresponding to N20 in the amino acid sequence as shown in SEQ ID NO: 1 may be preferably glycine, proline, aspartic acid, glutamic acid, threonine, alanine, valine, histidine, arginine, methionine, or isoleucine, more preferably glycine, proline, aspartic acid, glutamic acid, threonine, or alanine, further preferably glycine, proline, aspartic acid, or glutamic acid, still further preferably glycine or proline, and particularly preferably glycine.

Under the condition (e1), in particular, an amino acid residue corresponding to S22 in the amino acid sequence as shown in SEQ ID NO: 1 may be preferably valine.

It is preferable that the polypeptide according to one or more embodiments of the present invention at least satisfies the condition (d1).

The amino acid sequence of the polypeptide according to one or more embodiments of the present invention preferably satisfies at least one of the conditions (i), (f), and (g) described below, and particularly preferably satisfies at least either the condition (f) or (g), so that the amino acid residue corresponding to N33 in the amino acid sequence as shown in SEQ ID NO: 1 would not be modified with the N-linked sugar chain:

(i) an amino acid residue corresponding to N33 in the amino acid sequence as shown in SEQ ID NO: 1 is not asparagine;

(f) an amino acid residue corresponding to serine 34 (S34) in the amino acid sequence as shown in SEQ ID NO: 1 is proline; and (g) an amino acid residue corresponding to threonine 35 (T35) in the amino acid sequence as shown in SEQ ID NO: 1 is not serine or threonine. When such polypeptide is to be obtained via secretory production with the use of a polypeptide expression system comprising a yeast host, a polypeptide comprising an amino acid sequence in which an amino acid residue corresponding to N33 in the amino acid sequence as shown in SEQ ID NO: 1 is not modified with the N-linked sugar chain is obtained, and endonuclease activity in the culture supernatant containing such polypeptide is sufficiently high.

The condition (g) may be preferably a condition (g1): an amino acid residue corresponding to T35 in the amino acid sequence as shown in SEQ ID NO: 1 is lysine, valine, arginine, or leucine.

When the polypeptide according to one or more embodiments of the present invention satisfies at least either the condition (f) or (g1), endonuclease activity in the culture supernatant containing the polypeptide is particularly high when the polypeptide is obtained via secretory production using a polypeptide expression system comprising a yeast host.

Under the condition (g1), in particular, an amino acid residue corresponding to T35 in the amino acid sequence as shown in SEQ ID NO: 1 may be preferably lysine.

It is preferable that the polypeptide according to one or more embodiments of the present invention at least satisfy the condition (f).

More specific embodiments of the polypeptide according to one or more embodiments of the present invention include:

(Xp) a polypeptide comprising (or consisting of) an amino acid sequence derived from the amino acid sequence as shown in SEQ ID NO: 1 by introduction of at least one mutation selected from among (d2), (h2), and (e2) described below, and preferably at least either (d2) or (e2):

(d2) substitution of N20 with an amino acid residue other than asparagine, (h2) substitution of V21 with proline, and (e2) substitution of S22 with an amino acid residue other than serine or threonine; and at least one mutation selected from among (i2), (f2), and (g2) described below, and preferably at least either (f2) or (g2):

(i2) substitution of N33 with an amino acid residue other than asparagine, (f2) substitution of S34 with proline, and (g2) substitution of T35 with an amino acid residue other than serine or threonine; and (Yp) a polypeptide comprising (or consisting of) an amino acid sequence derived from the amino acid sequence of the polypeptide (Xp) by substitution, deletion, and/or addition of one or a plurality of amino acid residues, in addition to the mutations defined in (Xp) above, with the polypeptide (Xp) being more preferable. Such polypeptide is obtained via secretory production in the form of a polypeptide comprising an amino acid sequence in which neither of the amino acid residues corresponding to N20 and N33 in the amino acid sequence as shown in SEQ ID NO: 1 are modified with the N-linked sugar chain when obtained via secretory production using the polypeptide expression system comprising a yeast host, and endonuclease activity of the culture supernatant containing the polypeptide is sufficiently high. The term "one or a plurality of" used in (Yp) above is, for example, 1 to 40, 1 to 35, 1 to 30, 1 to 25, 1 to 20, 1 to 15, 1 to 10, 1 to 7, 1 to 5, 1 to 4, 1 to 3, or 1 or 2.

Under the condition (d2), in addition, N20 in the amino acid sequence as shown in SEQ ID NO: 1 may be preferably substituted with the amino acid residue exemplified as a specific example of an amino acid residue corresponding to N20 in the amino acid sequence as shown in SEQ ID NO: 1 under the condition (d1) or according to one or more embodiments thereof.

Under the condition (e2), in addition, S22 in the amino acid sequence as shown in SEQ ID NO: 1 may be preferably substituted with the amino acid residue provided as a specific example of the amino acid residue corresponding to S22 in the amino acid sequence as shown in SEQ ID NO: 1 under the condition (e1) or according to one or more embodiments thereof.

Under the condition (g2), in addition, T35 in the amino acid sequence as shown in SEQ ID NO: 1 may be preferably substituted with the amino acid residue provided as a specific example of the amino acid residue corresponding to T35 in the amino acid sequence as shown in SEQ ID NO: 1 under the condition (g1) or according to one or more embodiments thereof.

According to the specific embodiment of the polypeptide according to one or more embodiments of the present invention, it is particularly preferable that at least the conditions (d2) and (f2) be satisfied.

The polypeptide according to one or more embodiments of the present invention may be in the form of a fusion polypeptide comprising an additional polypeptide conjugated to either or both of the N terminal and C terminal sides. Examples of other polypeptides include, but are not limited to, a signal peptide and a tag peptide. Specific examples of signal peptides are as described below. Examples of tag peptides include a tag peptide comprising a plurality of (e.g., 6 to 10) histidine residues and FLAG tag peptide.

3. Polynucleotide Comprising a Nucleotide Sequence Encoding the Polypeptide According to One or More Embodiments of the Present Invention One or more embodiments of the present invention also provide a polynucleotide comprising a nucleotide sequence encoding the polypeptide according to one or more embodiments of the present invention that satisfies the conditions (a), (b), and (c) above.

The polynucleotide according to one or more embodiments of the present invention is RNA or DNA, and preferably DNA. When the polynucleotide according to one or more embodiments of the present invention is RNA, the nucleotide sequence as shown in "SEQ ID NO: 5" referred to in (A1), (A2), (A3), (D), (H), (E), (I), (F), (G), (D1), (E1), (G1), (D2), (H2), (E2), (I2), (F2), and (G2) described below or a partial nucleotide sequence thereof is a nucleotide sequence of SEQ ID NO: 5 or a partial nucleotide sequence thereof in which T is substituted by U.

A nucleotide sequence encoding the amino acid sequence as shown in SEQ ID NO: 1 is, for example, a nucleotide sequence of positions 256 to 993 of SEQ ID NO: 5.

Examples of nucleotide sequences encoding the amino acid sequence (a1) or (a2) (hereafter, it may be referred to as "the nucleotide sequence according to one or more embodiments of the present invention") include the following nucleotide sequences:

(A1) a nucleotide sequence exhibiting 85% or higher sequence identity to the nucleotide sequence of positions 256 to 993 of SEQ ID No: 5;

(A2) a nucleotide sequence derived from the nucleotide sequence of positions 256 to 993 by substitution, deletion, and/or addition of one or a plurality of nucleotides:

(A3) a nucleotide sequence of a polynucleotide that can hybridize under stringent conditions to a polynucleotide comprising the nucleotide sequence of positions 256 to 993 of SEQ ID No: 5;

(A4) a nucleotide sequence derived from the nucleotide sequence (A1), (A2), or (A3) by introduction of a silent mutation (i.e., a nucleotide substitution that does not change an amino acid residue encoded) thereinto, or (A5) a nucleotide sequence comprising, as an exon, the nucleotide sequence (A1), (A2), (A3), or (A4) and an intron sequence intercalated therein.

A specific example thereof is the nucleotide sequence (A1), (A2), or (A3).

The nucleotide sequence (A1), (A2), (A3), (A4), or (A5), and, in particular, the nucleotide sequence (A1), (A2), or (A3) may be referred to as "the nucleotide sequence according to one or more embodiments of the present invention" herein.

In the nucleotide sequence (A1), sequence identity may be preferably 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99%⁰ or higher. The nucleotide sequence (A1) encodes a mutant sequence of the amino acid sequence as shown in SEQ ID NO: 1, and sequence identity between the nucleotide sequence (A1) and the nucleotide sequence of positions 256 to 993 as shown in SEQ ID NO: 1 is less than 100%.

In the nucleotide sequence (A2), the term "one or a plurality of" refers to, for example, 1 to 120, 1 to 105, 1 to 90, 1 to 75, 1 to 60, 1 to 45, 1 to 30, 1 to 21, 1 to 15, 1 to 12, 1 to 9, 1 to 6, 1 to 4, or 1 to 3, or 2 to 105, 2 to 90, 2 to 75, 2 to 60, 2 to 45, 2 to 30, 2 to 21, 2 to 15, 2 to 12, 2 to 9, 2 to 6, 2 to 4, or 2 or 3, or 2.

In the nucleotide sequence of positions 256 to 993 of SEQ ID NO: 5, a region of A313 to C315 corresponds to N20 in SEQ ID NO: 1, a region of G316 to T318 corresponds to V21 in SEQ ID NO: 1, a region of T319 to C321 corresponds to S22 in SEQ ID NO: 1, a region of A352 to C354 corresponds to N33 in SEQ ID NO: 1, a region of T355 to C357 corresponds to S34 in SEQ ID NO: 1, and a region of A358 to T360 corresponds to T35 in SEQ ID NO: 1.

In the nucleotide sequence (A1), (A2), (A3), (A4), or (A5), and, in particular, the nucleotide sequence (A1), (A2), or (A3) according to one or more embodiments of the present invention, amino acid residues encoded by nucleotides corresponding to A313 to C315 and A352 to C354 in the nucleotide sequence as shown in SEQ ID NO: 5 are not modified with the N-linked sugar chain. The term "nucleotides corresponding to A313 to C315 and A352 to C354 in the nucleotide sequence as shown in SEQ ID NO: 5" refers to nucleotides in the nucleotide sequence according to one or more embodiments of the present invention corresponding to A313 to C315 and A352 to C354 in the nucleotide sequence as shown in SEQ ID NO: 5, when the nucleotide sequence as shown in SEQ ID NO: 5 is aligned with the nucleotide sequence according to one or more embodiments of the present invention, so as to maximize the degree of nucleotide consistency therebetween. A specific method of alignment is as described with reference to sequence identity. The expression "nucleotides corresponding to Yn to Zm in the nucleotide sequence as shown in SEQ ID NO: 5" used herein refers to nucleotides in the nucleotide sequence according to one or more embodiments of the present invention corresponding to nucleotide Y at position n to nucleotide Z at position m in the nucleotide sequence as shown in SEQ ID NO: 5, when the nucleotide sequence as shown in SEQ ID NO: 5 is aligned with the nucleotide sequence according to one or more embodiments of the present invention, so as to maximize the degree of nucleotide consistency therebetween.

The nucleotide sequence according to one or more embodiments of the present invention preferably satisfies at least one of the conditions (D), (H), and (E) described below, and particularly preferably satisfies at least either the condition (D) or (E), so that the amino acid residue encoded by nucleotides corresponding to A313 to C315 in the nucleotide sequence as shown in SEQ ID NO: 5 would not be modified with the N-linked sugar chain:

(D) nucleotides corresponding to A313 to C315 in the nucleotide sequence as shown in SEQ ID NO: 5 encode an amino acid residue other than asparagine, (H) nucleotides corresponding to G316 to T318 in the nucleotide sequence as shown in SEQ ID NO: 5 encode proline, and (E) nucleotides corresponding to T319 to C321 in the nucleotide sequence as shown in SEQ ID NO: 5 encode an amino acid residue other than serine or threonine. When a polynucleotide comprising any of such nucleotide sequences is introduced into a polypeptide expression system comprising a yeast host so as to obtain a polypeptide encoded by the nucleotide sequence of interest via secretory production, the polypeptide comprising an amino acid sequence in which an amino acid residue corresponding to N20 in the amino acid sequence as shown in SEQ ID NO: 1 is not modified with the N-linked sugar chain is obtained via secretory production, and endonuclease activity in the culture supernatant containing such polypeptide is sufficiently high.

The condition (D) may be preferably a condition (D1): nucleotides corresponding to A313 to C315 in the nucleotide sequence as shown in SEQ ID NO: 5 encode glycine, proline, aspartic acid, glutamic acid, threonine, alanine, valine, histidine, arginine, methionine, isoleucine, leucine, cysteine, tyrosine, or phenylalanine.

The condition (E) may be preferably a condition (E1): nucleotides corresponding to T319 to C321 in the nucleotide sequence as shown in SEQ ID NO: 5 encode valine, alanine, or lysine.

When the nucleotide sequence according to one or more embodiments of the present invention satisfies at least either the condition (D1) or (E1), endonuclease activity in the culture supernatant containing the polypeptide is particularly high when the polynucleotide comprising the nucleotide sequence of one or more embodiments of the present invention is introduced into a polypeptide expression system comprising a yeast host to implement secretory production of the polypeptide encoded by the nucleotide sequence according to one or more embodiments of the present invention.

In one or more embodiments, under the condition (D1), in particular, nucleotides corresponding to A313 to C315 in the nucleotide sequence as shown in SEQ ID NO: 5 preferably encode glycine, proline, aspartic acid, glutamic acid, threonine, alanine, valine, histidine, arginine, methionine, or isoleucine, more preferably encode glycine, proline, aspartic acid, glutamic acid, threonine, or alanine, and particularly preferably encode glycine, proline, aspartic acid, or glutamic acid.

In one or more embodiments, under the condition (E1), in particular, nucleotides corresponding to T319 to C321 in the nucleotide sequence as shown in SEQ ID NO: 5 preferably encode valine.

It is preferable that the nucleotide sequence according to one or more embodiments of the present invention at least satisfy the condition (D1).

The nucleotide sequence according to one or more embodiments of the present invention preferably satisfies at least one of the conditions (I), (F), and (G) described below, and particularly preferably satisfies at least either the condition (F) or (G), so that the amino acid residue encoded by nucleotides corresponding to A352 to C354 in the nucleotide sequence as shown in SEQ ID NO: 5 would not be modified with the N-linked sugar chain:

(I) nucleotides corresponding to A352 to C354 in the nucleotide sequence as shown in SEQ ID NO: 5 encode an amino acid residue other than asparagine;

(F) nucleotides corresponding to T355 to C357 in the nucleotide sequence as shown in SEQ ID NO: 5 encode proline; and (G) nucleotides corresponding to A358 to T360 in the nucleotide sequence as shown in SEQ ID NO: 5 encode an amino acid residue other than serine or threonine. When a polynucleotide comprising any of such nucleotide sequences is introduced into a polypeptide expression system comprising a yeast host so as to obtain a polypeptide encoded by the nucleotide sequence of interest via secretory production, the polypeptide comprising an amino acid sequence in which an amino acid residue corresponding to N33 in the amino acid sequence as shown in SEQ ID NO: 1 is not modified with N-linked sugar chain is obtained via secretory production, and endonuclease activity in the culture supernatant containing such polypeptide is sufficiently high.

The condition (G) may be preferably a condition (G1): nucleotides corresponding to A358 to T360 in the nucleotide sequence as shown in SEQ ID NO: 5 encode lysine, valine, arginine, or leucine.

When the nucleotide sequence according to one or more embodiments of the present invention satisfies at least either the condition (F) or (G1), endonuclease activity in the culture supernatant containing the polypeptide is particularly high when the polynucleotide comprising the nucleotide sequence according to one or more embodiments of the present invention is introduced into a polypeptide expression system comprising a yeast host to implement secretory production of the polypeptide encoded by the nucleotide sequence according to one or more embodiments of the present invention.

In one or more embodiments, under the condition (G1), in particular, nucleotides corresponding to A358 to T360 in the nucleotide sequence as shown in SEQ ID NO: 5 preferably encode lysine.

It is preferable that the nucleotide sequence according to one or more embodiments of the present invention at least satisfy the condition (F).

The nucleotide sequence according to one or more embodiments of the present invention comprises (or consists of) any of the sequences (Xn), (Yn), (Zn), or (Wn) described below:

(Xn) a nucleotide sequence derived from the nucleotide sequence of nucleotides 256 to 993 of the nucleotide sequence as shown in SEQ ID NO: 5 by at least one substitution selected from among (D2), (H2), and (E2) described below, and preferably at least either the substitution (D2) or (E2):

(D2) substitution of A313 to C315 in the nucleotide sequence as shown in SEQ ID NO: 5 to encode an amino acid residue other than asparagine:

(H2) substitution of G316 to T318 in the nucleotide sequence as shown in SEQ ID NO: 5 to encode proline; and (E2) substitution of T319 to C321 in the nucleotide sequence as shown in SEQ ID NO: 5 to encode an amino acid residue other than serine or threonine; and by at least one substitution selected from among (I2), (F2), and (G2) described below, and preferably at least either substitution (F2) or (G2):

(I2) substitution of A352 to C354 in the nucleotide sequence as shown in SEQ ID NO: 5 to encode an amino acid residue other than asparagine:

(F2) substitution of T355 to C357 in the nucleotide sequence as shown in SEQ ID NO: 5 to encode proline, and (G2) substitution of A358 to T360 in the nucleotide sequence as shown in SEQ ID NO: 5 to encode an amino acid residue other than serine or threonine;

(Yn) a nucleotide sequence derived from the nucleotide sequence as defined as (Xn) by substitution, deletion, and/or addition of one or a plurality of nucleotides, in addition to the mutations defined in (Xn) above, and encoding a polypeptide that satisfies the conditions (a), (b), and (c) above;

(Zn) a nucleotide sequence derived from the nucleotide sequence as defined as (Xn) or (Yn) by introduction of a silent mutation (i.e., nucleotide substitution that does not change the amino acid residue to be encoded); or (Wn) a nucleotide sequence comprising, as an exon, the nucleotide sequence (Xn), (Yn), or (Zn) and an intron sequence intercalated therein. The nucleotide sequence according to one or more embodiments of the present invention preferably comprises (or consists of) the nucleotide sequence defined as (Xn) above. When a polynucleotide comprising any of such nucleotide sequences is introduced into a polypeptide expression system comprising a yeast host so as to obtain a polypeptide encoded by the nucleotide sequence of interest via secretory production, the polypeptide comprising an amino acid sequence in which amino acid residues corresponding to N20 and N33 in the amino acid sequence as shown in SEQ ID NO: 1 are not modified with the N-linked sugar chain is obtained via secretory production, and endonuclease activity in the culture supernatant containing such polypeptide is sufficiently high. In the nucleotide sequence (Yn), the term "one or a plurality of" refers to, for example, 1 to 120, 1 to 105, 1 to 90, 1 to 75, 1 to 60, 1 to 45, 1 to 30, 1 to 21, 1 to 15, 1 to 12, 1 to 9, 1 to 6, 1 to 4, or 1 to 3.

Under the condition (D2), in addition, A313 to C315 in the nucleotide sequence as shown in SEQ ID NO: 5 may be preferably substituted to encode the amino acid residue described as specific examples of amino acid residue encoded by nucleotides corresponding to A313 to C315 in the nucleotide sequence as shown in SEQ ID NO: 5 under the condition (D1) or preferable embodiments thereof.

Under the condition (E2), in addition. T319 to C321 in the nucleotide sequence as shown in SEQ ID NO: 5 may be preferably substituted to encode the amino acid residue described as specific examples of amino acid residue encoded by nucleotides corresponding to T319 to C321 in the nucleotide sequence as shown in SEQ ID NO: 5 under the condition (E1) or preferable embodiments thereof.

Under the condition (G2), in addition, nucleotides A358 to T360 in the nucleotide sequence as shown in SEQ ID NO:

5 may be preferably substituted to encode the amino acid residue described as specific examples of amino acid residue encoded by nucleotides corresponding to A358 to T360 in the nucleotide sequence as shown in SEQ ID NO: 5 under the condition (G1) or preferable embodiments thereof.

4. Vector

One or more embodiments of the present invention relate to a vector comprising a polynucleotide comprising a nucleotide sequence encoding the polypeptide according to one or more embodiments of the present invention and a signal peptide that enables secretion of the polypeptide from a yeast.

The vector according to one or more embodiments of the present invention is an artificially constructed nucleic acid molecule, and it generally comprises a heterologous nucleotide sequence in the nucleic acid molecule. The vector according to one or more embodiments of the present invention can be introduced into a yeast and used for yeast transformation.

The polynucleotide comprising a nucleotide sequence encoding the polypeptide according to one or more embodiments of the present invention contained in the vector as described above.

A signal peptide that enables secretion of the polypeptide according to one or more embodiments of the present invention from a yeast contained in the vector is not particularly limited. An example thereof is a mating factor α (MFα) derived from Saccharomyces cerevisiae. In addition, a signal sequence of Ogataea angusta acid phosphatase (PHO1), Komagataella pastoris acid phosphatase (PHO1), Saccharomyces cerevisiae invertase (SUC2), or Saccharomyces cerevisiae PLB1 can be used as a signal peptide that enables secretion of the polypeptide according to one or more embodiments of the present invention from a yeast.

In the vector according to one or more embodiments of the present invention, a polynucleotide comprising a nucleotide sequence encoding the signal peptide may be provided at the 5' terminus of a polynucleotide comprising a nucleotide sequence encoding the polypeptide according to one or more embodiments of the present invention. The vector according to one or more embodiments of the present invention may further comprise a nucleotide sequence encoding the tag peptide at either or both of the 5' terminus and the 3' terminus (for example at the 3' terminus) of the polynucleotide comprising a nucleotide sequence encoding the polypeptide according to one or more embodiments of the present invention.

A nucleotide sequence encoding the polypeptide according to one or more embodiments of the present invention and the signal peptide can be inserted into an expression cassette and included in the vector in that state. An "expression cassette" is an expression system that comprises a nucleotide sequence encoding the polypeptide according to one or more embodiments of the present invention and the signal peptide and brings the resultant to an expressible state as a polypeptide. In an "expressible state," the nucleotide sequence included in the expression cassette is provided under the control of an element necessary for gene expression, so that it can be expressed in a yeast host. Examples of the element necessary for gene expression include a promoter and a terminator.

The vector according to one or more embodiments of the present invention can be in the form of, for example, a cyclic vector, a linear vector, or an artificial chromosome.

The term "promoter" used herein refers to a nucleotide sequence region located upstream of the nucleotide sequence encoding the polypeptide according to one or more embodiments of the present invention and the signal peptide. In addition to RNA polymerase, various transcription regulatory factors involved in promotion or suppression of transcription bind to or act on the region, such RNA polymerase reads the template nucleotide sequence encoding the polypeptide according to one or more embodiments of the present invention and the signal peptide, and such polymerase synthesizes (transcribes) complementary RNA.

As a promoter for expressing a polypeptide, any promoter that can induce expression in the presence of a carbon source employed may be adequately used without particular limitation.

When a carbon source is methanol, examples of promoters for expressing polypeptides include, but are not particularly limited to, AOX1 (alcohol oxidase 1) promoter, AOX2 (alcohol oxidase 2) promoter, CAT promoter, DHAS promoter, FDH promoter, FMD promoter, GAP promoter, and MOX promoter.

When a carbon source is glucose or glycerol, examples of promoters for expressing polypeptides include, but are not particularly limited to, GAP promoter, TEF promoter, LEU2 promoter, URA3 promoter, ADE promoter, ADH1 promoter, and PGK1 promoter.

In the expression cassette of the vector according to one or more embodiments of the present invention, a terminator may be located downstream of the nucleotide sequences encoding the polypeptide and the signal peptide. An appropriate terminator can be selected in accordance with a promoter and a host yeast used. When an AOX1 promoter is used, for example, an AOX1 terminator can be used.

The vector according to one or more embodiments of the present invention can further comprise, for example, nucleotide sequences of a cloning site containing one or more restriction enzyme recognition sites, an overlap region for use of the In-fusion Cloning System (Clontech) or Gibson assembly System (New England Biolabs), and a selection marker gene (e.g., an auxotrophic complementary gene or drug-resistant gene). Specific examples of selection marker genes are provided below. The vector according to one or more embodiments of the present invention can further comprise an autonomous replication sequence (ARS), a centromeric DNA sequence, and a telomeric DNA sequence in accordance with a host.

When the vector according to one or more embodiments of the present invention is incorporated into chromosome DNA of the host, it is preferable that the vector further comprise a nucleotide sequence that is capable of homologous recombination with the target site within chromosome DNA (i.e., the recombination site). Identity between the nucleotide sequence of the recombination site and the nucleotide sequence of the target site within chromosome DNA may be preferably 70% or higher, more preferably 90% or higher, further preferably 95% or higher, and still further preferably 98% or higher. The nucleotide sequence length of the recombination site may be preferably 20 to 2,000 bp.

When the vector according to one or more embodiments of the present invention is a linear vector, the linear vector preferably comprises a pair of recombination sites provided separately at both terminuses of a polynucleotide fragment containing a nucleotide sequence region including the expression cassette (and other elements such as a selection marker gene, according to need). Either or both of the pair of recombination sites may be a partial nucleotide sequence constituting the 5'- or 3'-terminus within the region or a nucleotide sequence located outside of the 5'- or 3'-terminus of the region. Either or both of the pair of recombination sites may comprise the nucleotide sequence of the selection marker gene.

The pair of recombination sites of the linear vector may be more preferably a pair of a first recombination site comprising a 5'-terminal partial sequence of a nucleotide sequence homologous to a target site within chromosome DNA and a second recombination site comprising a 3'-terminal partial sequence of the homologous sequence. A linear vector having such pair of recombination sites at both terminuses can be formed by cleaving a cyclic vector comprising a polypeptide comprising a nucleotide sequence comprising the expression cassette (and other elements such as a selection marker gene, according to need) and a nucleotide sequence homologous to the target site within chromosome DNA at a position inside the homologous nucleotide sequence. A method of producing such a linear vector is not limited to a method of cleaving a cyclic vector, and it may be another technique, such as chemical synthesis. The homologous nucleotide sequence may be of a selection marker gene.

In general, the vector according to one or more embodiments of the present invention comprises a fragment of a polynucleotide comprising (or consisting of) a nucleotide sequence encoding the polypeptide and the signal peptide and one or a plurality of other functional polynucleotide fragments as mentioned above ligated to either or both of the terminuses through, for example, a restriction enzyme recognition site. In the vector according to one or more embodiments of the present invention, the nucleotide sequence encoding the polypeptide and the nucleotide sequence encoding the signal peptide (and the nucleotide sequence encoding the tag peptide if it is present) are preferably provided on a single polynucleotide fragment, so that these nucleotide sequences are translated as continuous fusion polypeptides without a shift in the polypeptide reading frame. The signal peptide may be cleaved from the fusion polypeptide via post-translational modification. The nucleotide sequences adjacent to each other may be in direct contact with each other, or a nucleotide sequence encoding a linker polypeptide may be present between the nucleotide sequences adjacent to each other. The linker polypeptide comprises, for example, 1 to 100 amino acid residues.

The vector according to one or more embodiments of the present invention may be provided with a polynucleotide fragment of the element necessary for gene expression, other functional polynucleotide fragment, and the like. In addition, a nucleic acid molecule to which such polynucleotide fragment can be inserted (e.g., a nucleic acid molecule comprising a cloning site with one or more restriction enzyme recognition sites to which such polynucleotide fragment can be inserted) is within the scope of the vector according to one or more embodiments of the present invention.

A method for producing the vector according to the present invention is not particularly limited. For example, total-synthesis, PCR, or a method involving the use of the In-Fusion cloning System (Clontech) or the Gibson Assembly System (New England Biolabs) can be employed.

5. Yeast

One or more embodiments of the present invention also relate to a yeast comprising a polynucleotide comprising a nucleotide sequence encoding the polypeptide according to one or more embodiments of the present invention and a signal peptide that enables secretion of the polypeptide from the yeast. The yeast according to one or more embodiments of the present invention can comprise the polynucleotide as a part of the vector according to one or more embodiments of the present invention.

Specific yeast species that can be used as hosts are as described above.

As a method of introducing the polynucleotide into a yeast; i.e., a method of transformation, a known method can be employed. Examples thereof include, but are not particularly limited to, electroporation, the lithium acetate method, and the spheroplast method. As a method of Komagataella pastoris transformation, for example, a method of electroporation described in *High efficiency transformation by electroporation of Pichia pastoris pretreated with lithium acetate and dithiothreitol* (Biotechniques, 2004 January; 36 (1): 152-4) is generally employed.

After transformation, a selection marker used to select the transformant is not particularly limited. For example, a vector comprising an auxotrophic complementary gene, such as URA3 gene, LEU2 gene, ADE1 gene, HIS4 gene, or ARG4 gene, is used as a selection marker gene, transformation is carried out using, as hosts, auxotrophic yeast strains of uracil, leucine, adenine, histidine, and arginine, and a transformant can be selected on the basis of recovery of the prototroph phenotype. When a vector comprising a drug resistant gene, such as G418 resistant gene, Zeocin™ resistant gene, or hygromycin resistant gene, is used as a selection marker gene, transformants can be selected based on resistance on a medium containing G418, Zeocin™, or hygromycin, respectively. An auxotrophic selection marker can be used when the selection marker is destructed in a host. According to need, the selection marker can be destructed in a host, and a method known to a person skilled in the art can be employed.

The yeast according to one or more embodiments of the present invention may be a transformant transformed with the use of the vector, or it may be a progeny cell of the transformant. The number of the vector copies to be introduced into a single yeast cell, which is a transformant, is not particularly limited. A single copy of the vector may be introduced into a cell, or two or more copies of the vector may be introduced into a cell. The single copy of the vector may be in the form of a cyclic vector, a linear vector, or an artificial chromosome, or it may be incorporated into the chromosome of the host. All the two or more copies of the vector may be in the form of a cyclic vector, a linear vector, or an artificial chromosome, or all the copies may be incorporated into the host chromosome. Alternatively, a part of the copies of the vector may be in the form of a cyclic vector, a linear vector, or an artificial chromosome, and the other part of them may be incorporated into the host chromosome. The two or more copies of the vector may comprise two or more copies of the identical vector or 1 or more copies of different vectors.

6. Method for Producing the Polypeptide According to One or More Embodiments of the Present Invention One or more embodiments of the present invention relate to a method for producing the polypeptide according to one or more embodiments of the present invention comprising a step of culturing the yeast described in 5, above.

The target polypeptide according to one or more embodiments of the present invention may be collected from a culture product of the yeast obtained in the step of culture described above. The term "culture product" used herein refers to, in addition to a culture supernatant, cultured cells or fractured cells. Since the yeast according to one or more embodiments of the present invention is capable of secretory production of the polypeptide extracellularly, a culture supernatant may be particularly preferable as a culture product. Specifically, a method for producing the polypeptide according to one or more embodiments of the present invention with the use of the yeast is preferably a method of culturing the yeast according to one or more embodiments of the present invention and accumulating the polypeptide in the culture supernatant.

Conditions for culturing the yeast are not particularly limited and adequate conditions may be determined in accordance with cells. Any culture medium can be used, provided that it contains nutrients that are assimilable by cells. A common medium comprising such nutrients can be used, and examples of nutrients include: carbon sources, for example, a sugar, such as glucose, sucrose, and maltose, organic acids, such as lactic acid, acetic acid, citric acid, and propionic acid, alcohols, such as methanol, ethanol, and glycerol, hydrocarbons, such as paraffin, oils, such as soybean oil and rapeseed oil, or mixture of any thereof; nitrogen sources, such as ammonium sulfate, ammonium phosphate, urea, yeast extract, meat extract, peptone, and corn steep liquor; and other nutrients, such as inorganic salts and vitamins. Culture can be carried out using a batch or continuous culture system.

When a yeast strain of *Pichia*, *Komagataella*, or *Ogataea* is used according to one or more embodiments of the present invention, one or more type of the carbon sources selected from among glucose, glycerol, and methanol may be used. Such carbon source may be present at an early stage of culture, or it may be added during culture.

Yeast culture can be performed under general conditions. For example, culture can be performed at a pH of 2.5 to 10.0 at a temperature of 10° C. to 48° C. under an aerobic atmosphere for 10 hours to 10 days.

The polypeptide according to one or more embodiments of the present invention can be collected from the culture product by selecting methods of purification in adequate combinations from among known methods. For example, a culture suspension containing the yeast according to one or more embodiments of the present invention and a medium is first subjected to centrifugation or filtration, and yeast cells are then removed from a liquid fraction; i.e., a culture supernatant. The culture supernatant is subjected to one or more techniques selected from among, for example, salting out (e.g., ammonium sulfate precipitation or sodium phosphate precipitation), solvent precipitation (e.g., a method of protein fraction precipitation using acetone or ethanol), dialysis, gel filtration chromatography, ion-exchange chromatography, hydrophobic chromatography, affinity chromatography, reversed-phase chromatography, and ultrafiltration. Thus, the polypeptide according to one or more embodiments of the present invention is collected from the culture supernatant.

In the culture product, the polypeptide according to one or more embodiments of the present invention is not modified with the N-linked sugar chain. In contrast, other polypeptide species expressed and secreted by a yeast are generally modified with the N-linked sugar chain. Accordingly, polypeptides with the N-linked sugar chain may be separated from polypeptides without the N-linked sugar chain in the culture product with the use of, for example, lectin or an antibody that recognizes the sugar chain. Thus, efficiency for collecting the target polypeptide according to one or more embodiments of the present invention can be enhanced.

EXAMPLES

Hereafter, one or more embodiments of the present invention are described in greater detail with reference to the examples. However, these examples are not intended to limit the scope of the present invention. A specific procedure of a recombinant DNA technique adopted in the following examples is described in the following literature: Molecular Cloning 2nd Edition (Cold Spring Harbor Laboratory Press, 1989); Current Protocols in Molecular Biology (Greene Publishing Associates and Wiley-Interscience).

In the following examples, a plasmid used for yeast transformation was prepared by introducing the vector into an *E. coli* DH5α competent cell (Takara Bio Inc.), and culturing the obtained transformant for amplification. A plasmid was prepared from a plasmid-carrying strain with the use of the QIAprep spin miniprep kit (QIAGEN).

The AOX1 promoter (SEQ ID NO: 2), the AOX1 terminator (SEQ ID NO: 3), and the HIS4 gene (SEQ ID NO: 4) used for vector construction were prepared via PCR using, as a template, a mixture of chromosome DNA of the *Komagataella pastoris* ATCC76273 strain (the nucleotide sequences are Accession Numbers FR839628 to FR839631 of the European Molecular Biology Laboratory (EMBL)).

Synthetic DNA of the wild-type endonuclease gene of *Serratia marcescens* (SEQ ID NO: 5) provided with a signal sequence of the prepro α mating factor (the MF sequence) (SEQ ID NO: 105) used for vector construction was prepared in accordance with the disclosed sequence information (Calsberg Res. Commun., vol. 54, pp. 17-27, 1989).

PCR was carried out with the use of, for example, Prime STAR HS DNA polymerase (Takara Bio Inc.) under the conditions described in the instructions. Chromosome DNA was prepared from the *Komagataella pastoris* ATCC76273 strain using, for example, Dr. GenTLE® (Takara Bio Inc.) under the conditions described in the instructions.

Comparative Example 1: Construction of Vector for Wild-type Endonuclease Expression A gene fragment comprising HindIII-BamHI-BglII-XbaI-EcoRI multiple cloning sites (SEQ ID NO: 6) was fully synthesized, and the resultant was inserted into the site between HindIII and EcoRI of pUC19 (Code No. 3219; Takara Bio Inc.) to construct pUC-1.

Also, a nucleic acid fragment comprising BamHI recognition sequences added to both terminuses of the AOX1 promoter was prepared via PCR using the chromosome DNA mixture as a template and Primer 1 (SEQ ID NO: 7) and Primer 2 (SEQ ID NO: 8). The fragment was treated with BamHI, and the resultant was inserted into the BamHI site of pUC-1 to construct pUC-Paox.

Subsequently, a nucleic acid fragment comprising XbaI recognition sequences added to both terminuses of the AOX1 promoter was prepared via PCR using the chromosome DNA mixture as a template and Primer 3 (SEQ ID NO: 9) and Primer 4 (SEQ ID NO: 10). The fragment was treated with XbaI, and the resultant was inserted into the XbaI site of pUC-Paox to construct pUC-PaoxTaox.

Subsequently, a nucleic acid fragment comprising EcoRI recognition sequences added to both terminuses of the HIS4 gene was prepared via PCR using the chromosome DNA mixture as a template and Primer 5 (SEQ ID NO: 11) and Primer 6 (SEQ ID NO: 12). The fragment was treated with EcoRI, and the resultant was inserted into the EcoRI site of pUC-PaoxTaox to construct pUC-PaoxTaoxHIS4.

Subsequently, a nucleic acid fragment comprising BglII recognition sequences added to both terminuses of the endonuclease gene with the MF sequence was prepared via PCR using the synthetic DNA as a template and Primer 7 (SEQ ID NO: 13) and Primer 8 (SEQ ID NO: 14). The fragment was treated with BglI, and the resultant was inserted into the BglII site of pUC-PaoxTaoxHIS4 to construct pUC-PaoxENTaoxHIS4. pUC-PaoxENTaoxHIS4 is designed so as to allow the wild-type endonuclease gene to undergo secretory expression under the control of the AOX1 promoter.

Comparative Example 2: Acquisition of Transformed Yeast

With the use of the vector for wild-type endonuclease expression constructed in Comparative Example 1, *Komagataella pastoris* was transformed in the manner described below.

A histidine-auxotrophic strain derived from the *Komagataella pastoris* ATCC76273 strain was seeded in 3 ml of YPD medium (1% yeast extract bacto (Difco), 2% polypeptone (Nihon Pharmaceutical Co., Ltd.), and 2% glucose), and agitation culture was performed at 30° C. overnight to obtain a preculture suspension. The resulting preculture suspension (500 µl) was seeded in 50 ml of YPD medium, agitation culture was performed until OD600 reached 1 to 1.5, the cells were collected (3000×g, 10 minutes, 20° C.), and the cells were resuspended in 10 ml of 50 mM potassium phosphate buffer (pH 7.5) containing 250 µl of 1 M DTT (final concentration: 25 mM).

The suspension was incubated at 30° C. for 15 minutes, the cells were collected (3000×g, 10 minutes, 20° C.), and the cells were washed with 50 ml of ice-cooled STM buffer (270 mM sucrose, 10 mM Tris-HCl, 1 mM magnesium chloride, pH 7.5). The cells were collected from the wash suspension (3000×g, 10 minutes, 4° C.), washed again with 25 ml of STM buffer, and then collected (3000×g, 10 minutes, 4° C.). In the end, the cells were suspended in 250 µl of ice-cooled STM buffer, and the resulting suspension was designated as a competent cell suspension.

With the use of the vector for wild-type endonuclease expression constructed in Comparative Example 1 (i.e., pUC-PaoxENTaoxHIS4), *E. coli* was transformed, the resulting transformant was cultured in 2 ml of ampicillin-containing 2YT medium (1.6% tryptone bacto (Difco), 1% yeast extract bacto (Difco), 0.5% sodium chloride, and 0.01% ampicillin sodium (Wako Pure Chemical Industries, Ltd.)), and pUC-PaoxENTaoxHIS4 was obtained from the cells using the QIAprep spin miniprep kit (QIAGEN). This plasmid was treated with SalI to prepare a linear vector cleaved at the SalI recognition sequence within the HIS4 gene.

The competent cell suspension (60 µl) was mixed with 1 µl of the linear pUC-PaoxENTaoxHIS4 solution, the mixture was introduced into an electroporation cuvette (Disposable Cuvette electrodes, inter-electrode distance: 2 mm, BM Equipment Co., Ltd.), electroporation was performed at 7.5 kV/cm, 25 µF, and 200Ω, the cells were suspended in 1 ml of YPD medium, and the suspension was allowed to stand at 30° C. for 1 hour. Thereafter, the cells were collected (3000×g, 5 minutes, 20° C.), suspended in 1 ml of YNB medium (0.67% Yeast Nitrogen Base without Amino Acids (Difco)), and then collected again (3000×g, 5 minutes, 20° C.). After the cells were resuspended in an adequate amount of YNB medium, the cell suspension was applied to a YNB selection agar plate (0.67% Yeast Nitrogen Base without Amino Acids (Difco), 1.5% agarose, and 2% glucose), cells grown via static culture at 30° C. for 3 days were selected, and a yeast strain expressing wild-type endonuclease was obtained.

Comparative Example 3: Culture of Transformed Yeast

The yeast strain expressing wild-type endonuclease obtained in Comparative Example 2 was seeded in 2 ml of BMGY medium (1% yeast extract bacto (Difco), 2% polypeptone (Nihon Pharmaceutical Co., Ltd.), 0.34% Yeast Nitrogen Base without Amino Acids and Ammonium Sulfate (Difco), 1% ammonium sulfate, 0.4 mg/l biotin, 100 mM potassium phosphate (pH 6.0), 1% glycerol, and 1% methanol), the resultant was subjected to agitation culture at 30° C. for 72 hours, and the culture supernatant was then collected via centrifugation (12,000 rpm, 5 minutes, 4° C.).

Comparative Example 4: SDS-PAGE of Culture Supernatant

The culture supernatant obtained in Comparative Example 3 was analyzed via SDS-PAGE. The culture supernatant (12 µl) was mixed with 3 µl of 5× sample buffer (0.25 M Tris-HCl (pH 6.8), 50% glycerol, 6.7% SDS, and 0.01% BPB), and the resultant was treated at 95° C. for 8 minutes. The sample and the molecular weight marker (Precision Plus Protein™ Dual Color Standards, Bio-Rad) were subjected to SDS-PAGE electrophoresis using e-PAGEL gel (E-R15L, ATTO). Thereafter, the gel was rinsed for 15 minutes, stained with a staining liquid (Bio-Safe CBB G-250 stain; Bio-Rad) for 30 minutes, and then decolored with water. As a result, 2 bands were observed at sites shifted toward a side indicating a molecular weight higher than the molecular weight deduced on the basis of the amino acid sequence (within the frame in Lane 1, FIG. 1). As a result of treatment of the culture supernatant with the N-linked sugar chain cleavage kit (Endo Hf, BioLabs), the 2 bands disappeared, and a single band was newly observed at a position indicating the molecular weight deduced on the basis of the amino acid sequence (within the frame in Lane 2, FIG. 1). The results demonstrate that when the wild-type endonuclease is secretory produced with the aid of a *Komagataella* yeast host, the endonuclease is modified with the N-linked sugar chain(s) at one or two sites.

Example 1: Construction of Vector for Expressing Mutant Endonuclease (1)

With the use of the synthetic gene of the wild-type endonuclease gene fused with the MF sequence as a template, the N20Q mutant gene was prepared via PCR. PCR was performed with the use of Primer 7 and Primer 9 (SEQ ID NO: 15) and Primer 10 (SEQ ID NO: 16) and Primer 8, PCR-amplified fragments were mixed with each other, and then another PCR was performed with the use of Primer 7 and Primer 8, and a DNA fragment comprising BglII recognition sequences added to both terminuses of the N20Q mutant gene fused with the MF sequence was prepared. The term "N20Q mutant" used herein refers to a mutant comprising an amino acid sequence derived from the amino acid sequence of the wild-type endonuclease as shown in SEQ ID NO: 1 by substitution of N20 with Q. The same applies hereinbelow.

Subsequently, this mutant gene was used as a template to prepare various mutant genes. At the outset, two PCRs were performed using the two primer sets (1st PCR-1 and 1st PCR-2) as shown in Table 1 respectively, and then the resulting fragments were mixed, the resulting mixture was used as a template to perform another PCR with the use of Primer 7 and Primer 8, and a DNA fragment comprising BglII recognition sequences at both terminuses of various mutant genes fused with the MF sequence was prepared.

The DNA fragment containing the mutant endonuclease gene prepared above was treated with BglII, the resultant was inserted into the BglII site of pUC-PaoxTaoxHIS4 prepared in Comparative Example 1, and vectors for expression of various mutant endonuclease genes fused with the MF sequence were thus constructed.

TABLE 1

| Mutant | Site of mutation 1 | Site of mutation 2 | | 1st PCR-1 | 1st PCR-2 | |
|---|---|---|---|---|---|---|
| Mutant 1 | N20Q | N33Q | Primer 7 | Primer 11 (SEQ ID NO: 17) | Primer 12 (SEQ ID NO: 18) | Primer 8 |
| Mutant 2 | N20Q | N33Y | " | Primer 13 (SEQ ID NO: 19) | Primer 14 (SEQ ID NO: 20) | " |
| Mutant 3 | N20Q | N33A | " | Primer 15 (SEQ ID NO: 21) | Primer 16 (SEQ ID NO: 22) | " |
| Mutant 4 | N20Q | S34P | " | Primer 17 (SEQ ID NO: 23) | Primer 18 (SEQ ID NO: 24) | " |
| Mutant 5 | N20Q | T35K | " | Primer 19 (SEQ ID NO: 25) | Primer 20 (SEQ ID NO: 26) | " |
| Mutant 6 | N20Q | T35V | " | Primer 21 (SEQ ID NO: 27) | Primer 22 (SEQ ID NO: 28) | " |
| Mutant 7 | N20Q | T35R | " | Primer 23 (SEQ ID NO: 29) | Primer 24 (SEQ ID NO: 30) | " |
| Mutant 8 | N20Q | T35L | " | Primer 25 (SEQ ID NO: 31) | Primer 26 (SEQ ID NO: 32) | " |
| Mutant 9 | N20Q | T35G | " | Primer 27 (SEQ ID NO: 33) | Primer 28 (SEQ ID NO: 34) | " |
| Mutant 10 | N20Q | T35Q | " | Primer 29 (SEQ ID NO: 35) | Primer 30 (SEQ ID NO: 36) | " |
| Mutant 11 | N20Q | T35F | " | Primer 31 (SEQ ID NO: 37) | Primer 32 (SEQ ID NO: 38) | " |
| Mutant 12 | N20Q | T35W | " | Primer 33 (SEQ ID NO: 39) | Primer 34 (SEQ ID NO: 40) | " |
| Mutant 13 | N20Q | T35N | " | Primer 35 (SEQ ID NO: 41) | Primer 36 (SEQ ID NO: 42) | " |
| Mutant 14 | N20Q | T35I | " | Primer 37 (SEQ ID NO: 43) | Primer 38 (SEQ ID NO: 44) | " |
| Mutant 15 | N20Q | T35E | " | Primer 39 (SEQ ID NO: 45) | Primer 40 (SEQ ID NO: 46) | " |
| Mutant 16 | N20Q | T35A | " | Primer 41 (SEQ ID NO: 47) | Primer 42 (SEQ ID NO: 48) | " |
| Mutant 17 | N20Q | T35H | " | Primer 43 (SEQ ID NO: 49) | Primer 44 (SEQ ID NO: 50) | " |
| Mutant 18 | N20Q | T35M | " | Primer 45 (SEQ ID NO: 51) | Primer 46 (SEQ ID NO: 52) | " |
| Mutant 19 | N20Q | T35D | " | Primer 47 (SEQ ID NO: 53) | Primer 48 (SEQ ID NO: 54) | " |
| Mutant 20 | N20Q | T35C | " | Primer 49 (SEQ ID NO: 55) | Primer 50 (SEQ ID NO: 56) | " |
| Mutant 21 | N20Q | T35P | " | Primer 51 (SEQ ID NO: 57) | Primer 52 (SEQ ID NO: 58) | " |
| Mutant 22 | N20Q | T35Y | " | Primer 53 (SEQ ID NO: 59) | Primer 54 (SEQ ID NO: 60) | " |

These mutants are double mutants each comprising N20Q mutation and a mutation of the wild-type endonuclease as shown in SEQ ID NO: 1.

Example 2: Construction of Vector for Expressing Mutant Endonuclease (2)

The expression vector for a mutant endonuclease fused with the MF sequence constructed in Example 1 (Mutant 5) was used as a template to perform two PCRs using the two primers sets (1st PCR-1 and 1st PCR-2) as shown in Table 2 respectively, and then the obtained fragments were mixed, the resulting mixture was used as a template to perform another PCR using Primer 7 and Primer 8, and a DNA fragment comprising BglII recognition sequences at both terminuses of various mutant endonuclease genes fused with the MF sequence was prepared.

A DNA fragment containing the mutant endonuclease gene prepared above was treated with BglII, the resultant was inserted into the BglII site of pUC-PaoxTaoxHIS4 prepared in Comparative Example 1, and vectors for expression of various endonuclease genes fused with the MF sequence were thus constructed.

TABLE 2

| Mutant gene | Site of mutation 1 | Site of mutation 2 | | 1st PCR-1 | 1st PCR-2 | |
|---|---|---|---|---|---|---|
| Mutant 23 | N20D | T35K | Primer 7 | Primer 55 (SEQ ID NO: 61) | Primer 56 (SEQ ID NO: 62) | Primer 8 |
| Mutant 24 | N20A | T35K | " | Primer 57 (SEQ ID NO: 63) | Primer 58 (SEQ ID NO: 64) | " |
| Mutant 25 | V21P | T35K | " | Primer 59 (SEQ ID NO: 65) | Primer 60 (SEQ ID NO: 66) | " |

TABLE 2-continued

| Mutant gene | Site of mutation 1 | Site of mutation 2 | 1st PCR-1 | | 1st PCR-2 | |
|---|---|---|---|---|---|---|
| Mutant 26 | S22V | T35K | " | Primer 61 (SEQ ID NO: 67) | Primer 62 (SEQ ID NO: 68) | " |
| Mutant 27 | S22A | T35K | " | Primer 63 (SEQ ID NO: 69) | Primer 64 (SEQ ID NO: 70) | " |
| Mutant 28 | S22K | T35K | " | Primer 65 (SEQ ID NO: 71) | Primer 66 (SEQ ID NO: 72) | " |

These mutants are double mutants each comprising a T35K mutation and a mutation introduced into a residue selected from among N20, V21, and S22 in the amino acid sequence of the wild-type endonuclease as shown in SEQ ID NO: 1.

Example 3: Construction of Vector for Expressing Mutant Endonuclease (3)

The expression vector for a mutant endonuclease fused with the MF sequence constructed in Example 1 (Mutant 4) was used as a template to perform two PCRs using the two primer sets (1st PCR-1 and 1st PCR-2) as shown in Table 3 respectively, and then the obtained fragments were mixed, the resulting mixture was used as a template to perform another PCR using Primer 7 and Primer 8, and a DNA fragment comprising BglII recognition sequences at both terminuses of various mutant endonuclease genes fused with the MF sequence was prepared.

A DNA fragment containing the mutant endonuclease gene prepared above was treated with BglII, the resultant was inserted into the BglII site of pUC-PaoxTaoxHIS4 prepared in Comparative Example 1, and vectors for expression of various endonuclease genes fused with the MF sequence were thus constructed.

TABLE 3

| Mutant gene | Site of mutation 1 | Site of mutation 2 | 1st PCR-1 | | | 1st PCR-2 | |
|---|---|---|---|---|---|---|---|
| Mutant 29 | N20G | S34P | Primer 7 | Primer 67 (SEQ ID NO: 73) | Primer 68 (SEQ ID NO: 74) | Primer 8 | |
| Mutant 30 | N20P | S34P | " | Primer 69 (SEQ ID NO: 75) | Primer 70 (SEQ ID NO: 76) | " | |
| Mutant 31 | N20D | S34P | " | Primer 55 (SEQ ID NO: 61) | Primer 56 (SEQ ID NO: 62) | " | |
| Mutant 32 | N20E | S34P | " | Primer 71 (SEQ ID NO: 77) | Primer 72 (SEQ ID NO: 78) | " | |
| Mutant 33 | N20T | S34P | " | Primer 73 (SEQ ID NO: 79) | Primer 74 (SEQ ID NO: 80) | " | |
| Mutant 34 | N20A | S34P | " | Primer 57 (SEQ ID NO: 63) | Primer 58 (SEQ ID NO: 64) | " | |
| Mutant 35 | N20V | S34P | " | Primer 75 (SEQ ID NO: 81) | Primer 76 (SEQ ID NO: 82) | " | |
| Mutant 36 | N20H | S34P | " | Primer 77 (SEQ ID NO: 83) | Primer 78 (SEQ ID NO: 84) | " | |
| Mutant 37 | N20R | S34P | " | Primer 79 (SEQ ID NO: 85) | Primer 80 (SEQ ID NO: 86) | " | |
| Mutant 38 | N20M | S34P | " | Primer 81 (SEQ ID NO: 87) | Primer 82 (SEQ ID NO: 88) | " | |
| Mutant 39 | N20I | S34P | " | Primer 83 (SEQ ID NO: 89) | Primer 84 (SEQ ID NO: 90) | " | |
| Mutant 40 | N20L | S34P | " | Primer 85 (SEQ ID NO: 91) | Primer 86 (SEQ ID NO: 92) | " | |
| Mutant 41 | N20C | S34P | " | Primer 87 (SEQ ID NO: 93) | Primer 88 (SEQ ID NO: 94) | " | |
| Mutant 42 | N20Y | S34P | " | Primer 89 (SEQ ID NO: 95) | Primer 90 (SEQ ID NO: 96) | " | |

TABLE 3-continued

| Mutant gene | Site of mutation 1 | Site of mutation 2 | 1st PCR-1 | | 1st PCR-2 | |
|---|---|---|---|---|---|---|
| Mutant 43 | N20F | S34P | " | Primer 91 (SEQ ID NO: 97) | Primer 92 (SEQ ID NO: 98) | " |
| Mutant 44 | N20W | S34P | " | Primer 93 (SEQ ID NO: 99) | Primer 94 (SEQ ID NO: 100) | " |
| Mutant 45 | N20S | S34P | " | Primer 95 (SEQ ID NO: 101) | Primer 96 (SEQ ID NO: 102) | " |
| Mutant 46 | N20K | S34P | " | Primer 97 (SEQ ID NO: 103) | Primer 98 (SEQ ID NO: 104) | " |

These mutants are double mutants each comprising an S34P mutation and a mutation introduced into the N20 residue in the amino acid sequence of the wild-type endonuclease as shown in SEQ ID NO: 1.

Example 4: Preparation of Transformed Yeast

With the use of the vectors for expressing mutant endonuclease fused with the MF sequences constructed in Examples 1 to 3, *Komagataella pastoris* was transformed in the same manner as described in Comparative Example 2.

*E. coli* strains were transformed using the vectors for expressing mutant endonuclease constructed in Examples 1 to 3, the resulting transformants were cultured in 2 ml of ampicillin-containing 2YT medium, and a plasmid was obtained from the cells. The plasmid was treated with SalI and linearized.

Preparation of competent cells, transformation, and selection of transformants were performed in accordance with the methods described in Comparative Example 2.

Example 5: Culture of Transformed Yeast

The mutant endonuclease-expressing yeast strain obtained in Example 4 was cultured by the method described in Comparative Example 3, and the culture supernatant was collected.

Example 6: Measurement of Nuclease Activity in Culture Supernatant

Nuclease activity of the mutant endonuclease-expressing yeast strain obtained in Example 5 in the culture supernatant was measured in the manner described below.

A reaction buffer (2 ml; 20 mM Tris-HCl (pH 8.0), 1 mM $MgCl_2$, and 1 mM $CaCl_2$) was incubated at 37° C., 10 µl of the salmon sperm DNA solution (Invitrogen) and 10 µl of the diluted culture supernatant were added thereto, and a change in the absorbance at 260 nm was measured using a spectrophotometer (U-2900, HITACHI) in the time scan mode.

On the basis of the change in the absorbance at 260 nm 1 minute after the initiation of the reaction, nuclease activity in the culture suspension was determined. A nuclease activity unit is an activity of improving the absorbance at 260 nm by 1.0 within a period of 30 minutes.

TABLE 4

| Mutant | Site of mutation 1 | Site of mutation 2 | Nuclease activity (U/ml) |
|---|---|---|---|
| Mutant 1 | N20Q | N33Q | 8 |
| Mutant 2 | N20Q | N33Y | 12 |
| Mutant 3 | N20Q | N33A | 8 |
| Mutant 4 | N20Q | S34P | 3377 |
| Mutant 5 | N20Q | T35K | 2472 |
| Mutant 6 | N20Q | T35V | 1166 |
| Mutant 7 | N20Q | T35R | 1005 |
| Mutant 8 | N20Q | T35L | 965 |
| Mutant 9 | N20Q | T35G | 724 |
| Mutant 10 | N20Q | T35Q | 543 |
| Mutant 11 | N20Q | T35F | 523 |
| Mutant 12 | N20Q | T35W | 482 |
| Mutant 13 | N20Q | T35N | 362 |
| Mutant 14 | N20Q | T35I | 302 |
| Mutant 15 | N20Q | T35E | 221 |
| Mutant 16 | N20Q | T35A | 201 |
| Mutant 17 | N20Q | T35H | 157 |
| Mutant 18 | N20Q | T35M | 145 |
| Mutant 19 | N20Q | T35D | 84 |
| Mutant 20 | N20Q | T35C | 84 |
| Mutant 21 | N20Q | T35P | 24 |
| Mutant 22 | N20Q | T35Y | 16 |
| Mutant 23 | N20D | T35K | 3377 |
| Mutant 24 | N20A | T35K | 3377 |
| Mutant 25 | V21P | T35K | 12 |
| Mutant 26 | S22V | T35K | 1809 |
| Mutant 27 | S22A | T35K | 1327 |
| Mutant 28 | S22K | T35K | 1085 |
| Mutant 29 | N20G | S34P | 6271 |
| Mutant 30 | N20P | S34P | 5548 |
| Mutant 31 | N20D | S34P | 5065 |
| Mutant 32 | N20E | S34P | 5065 |
| Mutant 33 | N20T | S34P | 4583 |
| Mutant 34 | N20A | S34P | 4342 |
| Mutant 35 | N20V | S34P | 3859 |
| Mutant 36 | N20H | S34P | 3177 |
| Mutant 37 | N20R | S34P | 3136 |
| Mutant 38 | N20M | S34P | 3136 |
| Mutant 39 | N20I | S34P | 2412 |
| Mutant 40 | N20L | S34P | 1930 |
| Mutant 41 | N20C | S34P | 1688 |
| Mutant 42 | N20Y | S34P | 1206 |
| Mutant 43 | N20F | S34P | 1206 |
| Mutant 44 | N20W | S34P | 543 |
| Mutant 45 | N20S | S34P | 241 |
| Mutant 46 | N20K | S34P | 12 |

High-level nuclease activity was observed in the culture supernatants of various mutant endonuclease-expressing strains.

Example 7: SDS-PAGE of Culture Supernatant

The culture supernatant obtained in Example 5 was analyzed via SDS-PAGE. Analysis was performed in the same manner as in Comparative Example 4.

Figure 2:
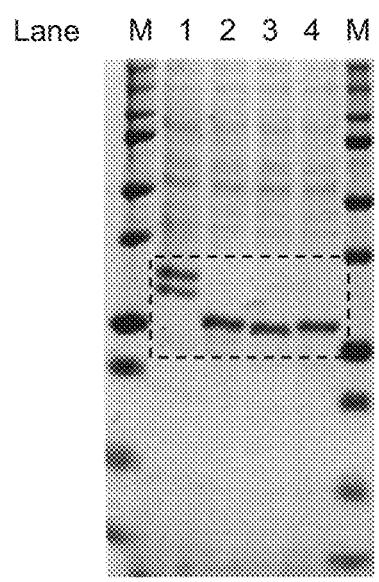
FIG. 2 shows the results of electrophoresis of a wild-type endonuclease secreted in a yeast culture supernatant (lane 1) and of mutant polynucleotides (lanes 2, 3, and 4).

Unlike the wild-type endonuclease (within the frame, lane 1, FIG. 2), various mutant endonucleases were found to show specific bands at positions corresponding to the deduced molecular weights (within the frame, lanes 2, 3, and 4, FIG. 2; each corresponding to the mutants 29, 30, and 31) and found to be secreted without the N-glycosylated modification.

Example 8: Measurement of Nuclease Activity in Culture Supernatant

The expression vector for a mutant endonuclease fused with the MF sequence constructed in Example 3 (Mutant 29) was used as a template to perform PCR using the Primer 7 and Primer 99 (SEQ ID NO: 106), the obtained fragment was treated with BglII, the resultant was inserted into the BglII site of pUC-PaoxTaoxHIS4 prepared in Comparative Example 1, and a vector for expression of His tag fusion gene of the mutant endonuclease provided with the MF sequence were thus constructed.

This mutant comprises, in addition to mutations in N20G and S34P, His tag (histidine 6) has been fused to the C terminus. With the use of the expression vector, *Komagataella pastoris* was transformed in the same manner as in Comparative Example 2. The resulting mutant endonuclease-expressing yeast was cultured by the method described in Comparative Example 3, and the culture supernatant was collected. As a result of measurement of nuclease activity in the culture supernatant by the method described in Example 6, it was found that activity equivalent to that of Mutant 29 without a His tag could be achieved, as shown in Table 5.

TABLE 5

| Mutant | Site of mutation 1 | Site of mutation 2 | Nuclease activity (U/ml) | Remarks |
|---|---|---|---|---|
| Mutant 47 | N20G | S34P | 5644 | His tag fusion |

All publications, patents, and patent applications cited herein are incorporated herein by reference in their entirety.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A polypeptide comprising
an amino acid sequence having at least 90% sequence identity to the amino acid sequence of SEQ ID NO: 1 and
derived from the amino acid sequence of SEQ ID NO: 1 by substitution, deletion, and/or addition of one or more amino acid residues,
wherein a yeast host expressing the polypeptide in a secretory production system does not add an N-linked sugar chain to the polypeptide,
wherein the polypeptide has endonuclease activity,
wherein the polypeptide comprises at least one of:
an amino acid residue selected from the group consisting of glycine, proline, aspartic acid, glutamic acid, threonine, alanine, valine, histidine, arginine, methionine, isoleucine, leucine, cysteine, tyrosine, phenylalanine, glutamine, tryptophan, serine, and lysine at a position corresponding to N20 of SEQ ID NO: 1;
proline at a position corresponding to V21 of SEQ ID NO: 1; or
an amino acid residue selected from the group consisting of valine, alanine, and lysine at a position corresponding to S22 of SEQ ID NO: 1, and
wherein the polypeptide further comprises at least one of:
an amino acid residue selected from the group consisting of glutamine, tyrosine, and alanine at a position corresponding to N33 of SEQ ID NO: 1;
proline at a position corresponding to S34 of SEQ ID NO: 1; or
an amino acid residue selected from the group consisting of lysine, valine, arginine, leucine, glycine, glutamine, phenylalanine, tryptophan, asparagine, isoleucine, glutamic acid, alanine, histidine, methionine, aspartic acid, cysteine, proline, and tyrosine at a position corresponding to T35 of SEQ ID NO: 1.

2. The polypeptide according to claim 1, wherein amino acid residues of the polypeptide corresponding to N20 and N33 of SEQ ID NO: 1 are not modified with the N-linked sugar chain.

3. The polypeptide according to claim 1,
wherein the polypeptide comprises at least one of:
an amino acid residue selected from the group consisting of glycine, proline, aspartic acid, glutamic acid, threonine, alanine, valine, histidine, arginine, methionine, isoleucine, leucine, cysteine, tyrosine, and phenylalanine at the position corresponding to N20 of SEQ ID NO: 1;
an amino acid residue selected from the group consisting of valine, alanine, and lysine at the position corresponding to S22 of SEQ ID NO: 1,
proline at the position corresponding to S34 of SEQ ID NO: 1; or
an amino acid residue selected from the group consisting of lysine, valine, arginine, and leucine at the position corresponding to T35 of SEQ ID NO: 1.

4. The polypeptide according to claim 1, wherein the sequence identity is 92% or more.

5. The polypeptide according to claim 1, wherein the sequence identity is 95% or more.

6. The polypeptide according to claim 1, wherein the sequence identity is 98% or more.

7. The polypeptide according to claim 1,
wherein the polypeptide comprises: an amino acid residue selected from the group consisting of glycine, proline, aspartic acid, glutamic acid, threonine, alanine, valine, histidine, arginine, methionine, and isoleucine at the position corresponding to N20 of SEQ ID NO: 1; or valine at the position corresponding to S22 of SEQ ID NO: 1, and
wherein the polypeptide further comprises: proline at the position corresponding to S34 of SEQ ID NO: 1; or lysine at the position corresponding to T35 of SEQ ID NO: 1.

8. The polypeptide according to claim 7, wherein the amino acid residue at the position corresponding to N20 of SEQ ID NO: 1 is selected from the group consisting of glycine, proline, aspartic acid, glutamic acid, threonine, and alanine.

9. The polypeptide according to claim 7, wherein the amino acid residue at the position corresponding to N20 of SEQ ID NO: 1 is selected from the group consisting of glycine, proline, aspartic acid, and glutamic acid.

* * * * *